US011234965B2

(12) United States Patent
Demopulos et al.

(10) Patent No.: US 11,234,965 B2
(45) Date of Patent: Feb. 1, 2022

(54) ANTI-INFLAMMATORY AND MYDRIATIC INTRACAMERAL SOLUTIONS FOR INHIBITION OF POSTOPERATIVE OCULAR INFLAMMATORY CONDITIONS

(71) Applicant: Omeros Corporation, Seattle, WA (US)

(72) Inventors: Gregory A. Demopulos, Mercer Island, WA (US); Vincent A. Florio, Seattle, WA (US)

(73) Assignee: OMEROS CORPORATION, Seattle, WA (US)

( * ) Notice: Subject to any disclaimer, the term of this patent is extended or adjusted under 35 U.S.C. 154(b) by 0 days.

(21) Appl. No.: 16/276,337

(22) Filed: Feb. 14, 2019

(65) Prior Publication Data

US 2019/0175552 A1   Jun. 13, 2019

Related U.S. Application Data

(63) Continuation of application No. 15/836,772, filed on Dec. 8, 2017, now abandoned, which is a continuation of application No. 14/953,806, filed on Nov. 30, 2015, now abandoned.

(60) Provisional application No. 62/086,133, filed on Dec. 1, 2014.

(51) Int. Cl.
| A61K 31/407 | (2006.01) |
| A61K 31/137 | (2006.01) |
| A61K 31/405 | (2006.01) |
| A61K 31/192 | (2006.01) |
| A61K 31/4174 | (2006.01) |
| A61K 9/00 | (2006.01) |

(52) U.S. Cl.
CPC .......... *A61K 31/407* (2013.01); *A61K 9/0048* (2013.01); *A61K 31/137* (2013.01); *A61K 31/192* (2013.01); *A61K 31/405* (2013.01); *A61K 31/4174* (2013.01)

(58) Field of Classification Search
CPC .............. A61K 2300/00; A61K 31/137; A61K 31/192; A61K 31/405; A61K 31/407; A61K 31/4174; A61K 9/0048; A61P 27/02; A61P 27/08; A61P 27/12; A61P 29/00; A61P 31/22; A61P 43/00
See application file for complete search history.

(56) References Cited

U.S. PATENT DOCUMENTS

| 4,474,751 A | 10/1984 | Haslam et al. |
| 4,474,811 A | 10/1984 | Masuda et al. |
| 4,550,022 A | 10/1985 | Garabedian et al. |
| 4,876,250 A | 10/1989 | Clark |
| 4,938,970 A | 7/1990 | Hustead et al. |
| 5,051,443 A | 9/1991 | Neufeld et al. |
| 5,110,493 A | 5/1992 | Cherng-Chyi et al. |
| 5,212,196 A | 5/1993 | House et al. |
| 5,298,487 A | 3/1994 | Chen et al. |
| 5,371,078 A | 12/1994 | Clark et al. |
| 5,523,316 A | 6/1996 | Gan et al. |
| 5,587,175 A | 12/1996 | Viegas et al. |
| 5,612,027 A | 3/1997 | Galin et al. |
| 5,624,893 A | 4/1997 | Yanni |
| 5,696,091 A | 12/1997 | York et al. |
| 5,759,532 A | 6/1998 | Galin et al. |
| 5,767,105 A | 6/1998 | Peyman |
| 5,798,356 A | 8/1998 | Doshi |
| 5,800,385 A | 9/1998 | Demopulos et al. |
| 5,811,446 A | 9/1998 | Thomas |
| 5,820,583 A | 10/1998 | Demopulos et al. |
| 5,858,017 A | 1/1999 | Demopulos et al. |
| 5,860,950 A | 1/1999 | Demopulos et al. |
| 5,972,326 A | 10/1999 | Galin et al. |
| 6,030,974 A | 2/2000 | Schwartz et al. |
| 6,056,715 A | 5/2000 | Demopulos et al. |
| 6,117,907 A | 9/2000 | Sher |
| 6,210,394 B1 | 4/2001 | Demopulos et al. |
| 6,218,428 B1 | 4/2001 | Chynn |
| 6,242,447 B1 | 6/2001 | Demopulos et al. |
| 6,254,585 B1 | 7/2001 | Demopulos et al. |
| 6,261,279 B1 | 7/2001 | Demopulos et al. |
| 6,280,745 B1 | 8/2001 | Flore et al. |
| 6,350,781 B1 | 2/2002 | Shahinia |
| 6,395,746 B1 | 5/2002 | Cagle et al. |
| 6,413,961 B1 | 7/2002 | Demopulos et al. |
| 6,420,432 B2 | 7/2002 | Demopulos et al. |

(Continued)

FOREIGN PATENT DOCUMENTS

| AU | 2009248461 | 7/2013 |
| CN | 101327325 A | 12/2008 |

(Continued)

OTHER PUBLICATIONS

Lindstrom et al. (Clinical Ophthalmology, 2014, 8, 1735-1744), (Year: 2014).*
FDA document (Omidria, FDA, May 2014) (Year: 2014).*
Grob (Clinical Ophthalmology, 2014, 8, 1281-89) (Year: 2014).*
Gaudana, The AAPS J vol. 12, Sep. 3, 2010 (Year: 2010).*
Database WPI Week 200256, Derwent Publications Ltd., London, GB: AN 2002-523513 & JP 2002 161032 A, Tasisho Pharm Co. Ltd, Jun. 4, 2002. Abstract Only.
Database WPI Week 200239; Derwent Publications Ltd., London, GB; AN 2002-362397 XP002478749 & WO 02/24191 A, Yong Guang Pharm Co Ltd, Mar. 28, 2002. Abstract Only.

(Continued)

*Primary Examiner* — Umamaheswari Ramachandran
(74) *Attorney, Agent, or Firm* — Anna S. Gall, Esq.; Tineka J. Quinton, Esq.

(57) ABSTRACT

The present invention provides methods for inhibiting postoperative inflammatory conditions following ophthalmologic surgical procedures by administering intraocularly during an ophthalmologic surgical procedure a solution including a nonsteroidal anti-inflammatory agent and an alpha-1 adrenergic mydriatic agent, such as a liquid irrigation solution of ketorolac and phenylephrine.

6 Claims, 7 Drawing Sheets

(56) References Cited

U.S. PATENT DOCUMENTS

Figure 1:
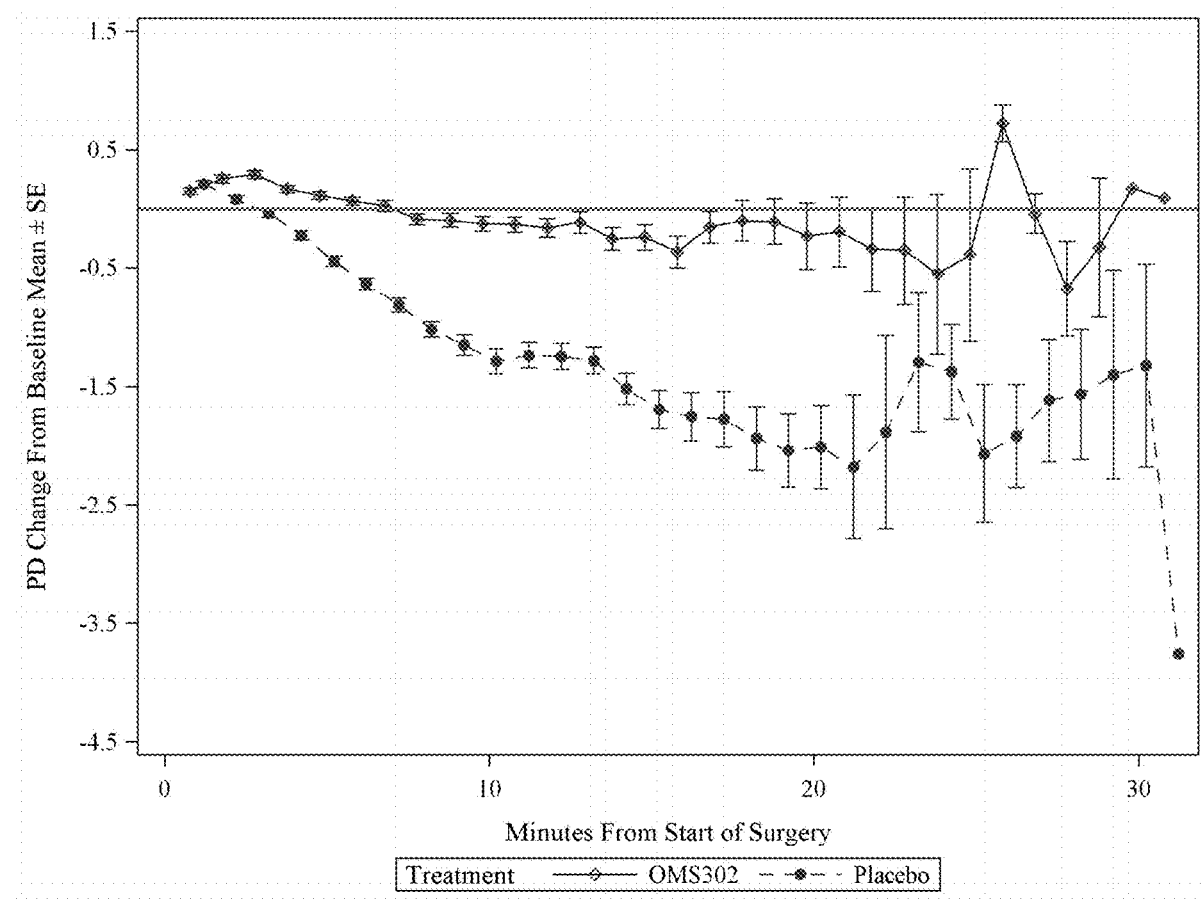

| | | |
|---|---|---|
| 6,492,332 B1 | 12/2002 | Demopulos et al. |
| 6,495,598 B1 | 12/2002 | Yoneda et al. |
| 6,562,873 B2 | 5/2003 | Olejnik et al. |
| 6,645,168 B2 | 11/2003 | Demopulos et al. |
| 7,091,181 B2 | 8/2006 | Demopulos et al. |
| 7,842,714 B2 | 11/2010 | Farnes et al. |
| 7,973,068 B2 | 7/2011 | Demopulos et al. |
| 8,173,707 B2 | 5/2012 | Demopulos et al. |
| 8,586,633 B2 | 11/2013 | Demopulos et al. |
| 9,066,856 B2 | 6/2015 | Demopulos et al. |
| 9,278,101 B2 | 3/2016 | Demopulos et al. |
| 9,399,040 B2 | 7/2016 | Demopulos et al. |
| 9,486,406 B2 | 11/2016 | Demopulos et al. |
| 9,585,895 B2 | 3/2017 | Demopulos et al. |
| 9,855,246 B2 | 1/2018 | Demopulos et al. |
| 2002/0071874 A1 | 6/2002 | Olejnik et al. |
| 2002/0128267 A1 | 9/2002 | Bandyopadhyay et al. |
| 2002/0183279 A1 | 12/2002 | Tanaka |
| 2003/0017199 A1 | 1/2003 | Woodward et al. |
| 2003/0087962 A1 | 5/2003 | Demopulos et al. |
| 2003/0096807 A1 | 5/2003 | Demopulos et al. |
| 2003/0191187 A1 | 10/2003 | Lee et al. |
| 2004/0072809 A1 | 4/2004 | Demopulos et al. |
| 2009/0227534 A1 | 9/2009 | Garcia-Salgado Lopez et al. |
| 2010/0087503 A1 | 4/2010 | Farnes et al. |
| 2010/0311688 A1 | 12/2010 | Chapin et al. |
| 2010/0311705 A1 | 12/2010 | Demopulos et al. |
| 2011/0105450 A1 | 5/2011 | Chapin et al. |
| 2012/0022094 A1 | 1/2012 | Harris et al. |
| 2013/0079344 A1 | 3/2013 | Demopulos et al. |
| 2014/0221326 A1 | 8/2014 | Demopulos et al. |
| 2014/0235597 A1 | 8/2014 | Demopulos et al. |
| 2014/0235691 A1 | 8/2014 | Demopulos et al. |
| 2015/0119440 A1* | 4/2015 | Karolchyk ......... A61K 31/4409 514/413 |
| 2015/0342928 A1 | 12/2015 | Demopulos et al. |
| 2016/0106761 A1 | 4/2016 | Demopulos et al. |
| 2016/0279099 A1 | 9/2016 | Demopulos et al. |
| 2017/0100412 A1 | 4/2017 | Demopulos et al. |
| 2017/0182007 A1 | 6/2017 | Demopulos et al. |
| 2017/0196838 A1 | 7/2017 | Demopulos et al. |
| 2017/0246150 A1 | 8/2017 | Demopulos et al. |
| 2017/0312295 A1 | 11/2017 | Demopulos et al. |
| 2018/0085349 A1 | 3/2018 | Demopulos et al. |

FOREIGN PATENT DOCUMENTS

| | | |
|---|---|---|
| CN | 103143022 A | 6/2013 |
| CN | 104856990 A | 8/2015 |
| EP | 0364266 A2 | 4/1990 |
| EP | 0 550 921 A1 | 7/1993 |
| EP | 0550921 | 7/1993 |
| EP | 0 903 151 A1 | 3/1999 |
| JP | 9-506620 | 6/1995 |
| JP | 2001-516258 | 9/2001 |
| JP | 2002161032 A2 | 6/2002 |
| WO | WO 87/07141 | 12/1987 |
| WO | WO 91/02527 | 3/1991 |
| WO | WO 92/04008 | 3/1992 |
| WO | WO 94/08602 | 4/1994 |
| WO | WO 95/09003 | 4/1995 |
| WO | WO 95/16435 | 6/1995 |
| WO | WO1995014478 A1 | 6/1995 |
| WO | WO 95/34298 | 12/1995 |
| WO | WO 96/00055 | 1/1996 |
| WO | WO 96/19233 | 6/1996 |
| WO | WO 97/009973 | 3/1997 |
| WO | WO 97/21445 | 6/1997 |
| WO | WO 98/38996 | 9/1998 |
| WO | WO 98/41171 | 9/1998 |
| WO | WO 98/47366 | 10/1998 |
| WO | WO 98/47890 | 10/1998 |
| WO | WO 00/01379 | 1/2000 |
| WO | WO 00/03705 | 1/2000 |
| WO | WO 00/23061 | 4/2000 |
| WO | WO 00/23062 | 4/2000 |
| WO | WO 00/23066 | 4/2000 |
| WO | WO 00/23072 | 4/2000 |
| WO | WO 00/25745 | 5/2000 |
| WO | WO 00/35433 | 6/2000 |
| WO | WO2000051620 A1 | 9/2000 |
| WO | WO 00/69255 | 11/2000 |
| WO | WO 01/07050 A1 | 1/2001 |
| WO | WO 01/41550 A2 | 6/2001 |
| WO | WO 01/82914 A2 | 11/2001 |
| WO | WO 02/05815 A1 | 1/2002 |
| WO | WO 02/24191 A1 | 3/2002 |
| WO | WO 02/09702 | 7/2002 |
| WO | WO 2004/010894 A2 | 2/2004 |
| WO | WO 2009/061431 A2 | 5/2009 |
| WO | WO 2009/111418 | 9/2009 |
| WO | WO2010102276 A2 | 9/2010 |
| WO | WO 2012/016000 A2 | 2/2012 |
| WO | WO 2013/020021 A1 | 2/2013 |
| WO | WO 2014/066485 A1 | 5/2014 |
| WO | WO 2016/089739 A2 | 6/2016 |

OTHER PUBLICATIONS

Corbett et al., "Intraocular adrenaline maintains mydriasis during cataract surgery," *Br. J. Ophthalmol.* 78:95-98 (1994).

Gillart et al., "Effects of Local Clonidine for Prolongation of Akinesia After Peribulbar Block," *Anesthesiology* 31(3A):A941-A942 (1994).

Grond, S., et al., "Inhibition of Synovial Plasma Extravasation by Preemptive Administration of an Antiinflammatory Irrigation Solution in the Rat Knee," *Anesth Analg* 92:1301-6 (2001).

Malhotra et al., "Comparison of the cardiovasculare effects of 2.5% phenylephrine and 10% phenylephrine during ophthalmic surgery," *Eye* 12:973-975 (1998).

Antcliff et al., "The maintenance of per-operative mydriasis in phacoemulsification with topical diclofenac sodium," *Eye* 11:389-391 (1997).

Liou, Shiow-Wen, et al., "The Effects of Intracameral Adrenaline Infusion on Pupil Size, Pulse Rate, and Blood Pressure During Phacoemulsification," *J Ocular Pharmacol Ther* 14(4):357-361 (1998).

Gimbel, "The effect of treatment with topical nonsteroidal anti-inflammatory drugs with and without intraoperative epinephrine on the maintenance of mydriasis during cataract surgery," *Ophthalmology* 96(5):585-588 (1989).

Shimada, H., et al., "Effects of Flubiprofen on Extracapsular Cataract Extraction," *Journal of the Eye* 4(5):719-722 (1987). Japanese language.

Shimada, H., et al., "Effects of Flubiprofen on Extracapsular Cataract Extraction," *Journal of the Eye* 4(5):719-722 (1987). English Translated copy.

Titcomb, "Revision of Pharmacology," www.optometry.co.uk 25-34 (2002).

Zimm, Jeffrey L., et al., "Effects of topical suprofen and flurbiprofen on the miosis produced by anterior chamber irrigation with cholinergic agonists," *J Cataract Refract Surg* 17:790-793 (1991).

Zimm, J.L., et al., "Effects of topical suprofen and flurbiprofen on the miosis produced by anterior chamber irrigation with cholinergic agonists," *J Cataract Refract Surg* 17:790-793 (1991).

Snyder, R.W., et al., "Acular as a single agent for use an an antimiotic and anti-inflammatory in cataract surgery," *J Cataract Refract Surg* 26(8):1225-1227 (2000).

Shimada, H., et al., "Effects of an Anti-prostaglandin Agent Added to the Irrigation Solution on Damage to the Anterior Segment in Monkey Eyes Induced by Pars Plana Vitrectomy," *Acta Soc Ophthalmol Jpn* 93:823-829 (1989). Japanese language with English abstract.

Miyake et al., "Latanoprost Accelerates Disruption of the Blood-Aqueous Barrier and the Incidence of Agiographic Cystoid Macular Edema in Early Postoperative Pseudophakias," *Arch Ophthalmol* 117:34-40 (1999).

Miyake et al., "Enhanced Disruption of the Blood-Aqueous Barrier and the Incidence of Angiographic Cystoid Macular Edema by

(56) References Cited

OTHER PUBLICATIONS

Topical Timolol and Its Preservative in Early Postoperative Pseudophakia," *Arch Ophthalmol* 119:387-394 (2001).
Fichman, "Anesthesia and preoperative and postoperative medications," *Current Opinion in Ophthalmology* 7:17-20 (1996).
Alcon Laboratories, "The Worldwide Winner TobraDex," Internet Publication, www.alconlabs.com/us/aj/products/RxTher/TobraDexPro.jhtml (Jun. 3, 2003).
Simone, J.N., "Comparison of the Efficacy and Safety of Ketorolac Tromethamine 0.5% and Prednisolone Acetate 1% after Cataract Surgery," *J Cataract Refract Surg.* 25(5):699-704 (1999).
Heier, J., et al., "Ketorolac tromethamine 0.5% ophthalmic solution in the treatment of moderate to severe ocular inflammation after cataract surgery: a randomized, vehicle-controlled clinical trial," *Am J Ophthalmol* 127(3):253-9 (1999).
Flach, A.J., et al., "The Effect of Ketorolac Tromethamine in Reducing Postoperative Inflammation: Double-Mask Parallel Comparison with Dexamethasone," *Annals of Ophthalmology* 21:407-411 (1989).
Alcon Laboratories, "Sterile Intraocular Irrigating Solution," Internet Publication, www.alconlabs.com/ca_en/aj/products/bss-pm1.jhtml (Jun. 26, 2003).
Wang, R.F., et al., "Effect of Oxymetazoline on Aqueous Humor Dynamics and Ocular Blood Flow in Monkeys and Rabbits," *Arch Ophthalmol* 111:535-8 (1993).
Chu, Teh-Ching, et al., "Oxymetazoline: Potential Mechanisms of Inhibitory Effects on Aqueous Humor Dynamics," *Pharmacology* 53:259-270 (1996).
Papa, V., et al., "Topical naproxen sodium for inhibition of miosis during cataract surgery. Prospective, randomized clinical trials," *Eye* 16(3):292-296 (2002).
Patil, Popat N., et al., "Antimuscarinic Action of Oxymetazoline on Human Intraocular Muscles," *Journal of Ocular Pharmacology and Therapeutics* 20(4):328-332 (2004).
Flach, A.J., et al., "Effectiveness of ketorolac tromethamine 0.5% ophthalmic solution for chronic aphakic and pseudophakic cystoid macular edema," *Am J Ophthalmol* 103(4):479-86 (1987).
Anderson, Janet A., et al., "Multiple Dosing Increases the Ocular Bioavailability of Topically Administered Flurbiprofen," *Arch Ophthalmol* 106:1107-1109 (1988).
Ishikawa, H., et al., "Comparison of post-junctional alpha-adrenoceptors in iris dilator muscle of humans, and albino and pigmented rabbits," *Naunyn Schmeidebergs Arch Pharmacol* 354(6):765-72 (1996).
Liou, Shiow-Wen, et al., "Maintenance of Mydriasis with One Bolus of Epinephrine Injection During Phacoemulsification," *J Ocular Pharmacol Ther* 17(3):249-253 (2001).
Bäckström G, "Behndig A.Redilatation with intracameral mydriatics in phacoemulsification surgery," *Acta Ophthalmol Scand.* 84(1):100-4 (2006).
Lundberg, Björn, M.D., et al., "Intracameral mydriatics in phacoemulsification cataract surgery," *J Cataract Refract Surg* 29:2366-2371 (2003).
Flach, Allan J., "Cyclo-oxygenase Inhibitors in Ophthalmology," *Survey of Ophthalmology* 36(4):259-284 (1992).
Flach, A.J., et al., "The effect of ketorolac tromethamine solution 0.5% in reducing postoperative inflammation after cataract extraction and intraocular lens implantation," *Ophthalmology* 95(9):1279-84 (1988).
Flach, Allan, J., "Corneal Melts Associated with Topically Applied Nonsteroidal Anti-Inflammatory Drugs," *Tr Am Opth* 99:205-212 (2001).
Perry, H.D., et al., "An update on the use of ophthalmic ketorolac tromethamine 0.4%," *Expert Opin Pharmacother.* 7(1):99-107 (2006).
"The Pocket Oxford American Dictionary of Current English," Oxford University Press, New York, p. 418 (2002).
"The Bantam Medical Dictionary," Laurence Urdang Associates Ltd., Bantam Books, New York, p. 17 (1981).
Gills, J.P., "Intraocular irrigating solutions with cataract surgery," *Atlas of Cataract Surgery*, Masket, Samuel MD and Crandall, Alan S MD, eds. Chapter 3, Martin Dunitz Publisher (1999).
Gills, J.P., et al., Comment on "Bacterial endophthalmitis prophylaxis," *Ophthalmology* 110(8):1668 (2003).
Gills, J.P., et al., "Effect of intracameral triamcinolene to control inflammation following cataract surgery," *J Cataract Refract Surg* 31(8):1670-1 (2005).
Gills, J.P., "My Method of Extracapsular Cataract Extraction With Implantation of a Posterior Chamber Intraocular Lens," *Ophthalmic Surgery* 16(6):386-392 (1985).
Hirowatari, Takeo, et al., "Evaluation of a New Preoperative Opthalmic Solution," *Can J Ophthalmol* 40:58-62 (2005).
Snyder, R.W., et al., "Acular as a single agent for use an an antimiotic and anti-inflammatory in cataract surgery," *J Cataract Refract Surg* 26:1225-127 (2000).
Srinivasan, M.S., et al., "Topical ketorolac tromethamine 0.5% versus diclofenac sodium 0.1% to inhibit miosis during cataract surgery," *J Cataract Refract Surg* 28:517-520 (2002).
*Taber's Cyclopedic Medical Dictionary*, 19$^{th}$ Edition, F.A. Davis Company, Philadelphia, pp. 1131-1132 (2003).
Eleftheriadis, H., et al., "Corneal toxicity secondary to inadvertent use of benzalkonium chloride preserved viscoelastic material in cataract surgery," *British Journal of Ophthalmology* 86:299-305 (2002).
Zaczek, A., et al., "The effect of phenylephrine on pain and flare intensity in eyes with uvitis," *Acta Ophthalmologica Scandinavica* 78:516-518 (2000).
Online Merck Manual Home Edition articles entitled, "Inflammation," "Blepharitis," "Dacrocystitis," "Infections," "Gout," "Pseudogout," "Sinusitis," "Pharyngitis," "Reiter's Syndrome," "Tongue Disorders," "Meningitis," "Viral Infections," "Hemrroids," "Urethritis," "Episcleritis," "Conjunctivitis," and "Rheumatoid Arthritis," www.merck.com/mmhe/print/sec20/ch236/ch236d.html, 51 pages, accessed Mar. 2007 (2003).
Medline Plus, Medical Encyclopedia: Neuroretinitis, Definition of "Neuroretinitis", www.nlm.nih.gov/medlineplus/ency/article/002268.htm, accessed Mar. 2007, (2005).
Kuby, J., "Immunology," Third Edition, W.H. Freeman and Company, New York, pp. 67 and 365-378, (1997).
Chaudhary, K.P., et al., "Preoperative Topical Flubiprofen—Na$^+$ in Extracapsular Lens Extraction Role in Maintaining Intraoperative Pupillary Dilation," *Ind. J. Opthal.* 40(4):109-114 (1992).
Arshinoff, S.A., et al., "Pharmacotherapy of Photorefractive Keratectomy," *J Cataract Refract Surg* 22:1037-1044 (1996).
Volpe, N, et al., "Single Dose Ondansetron for Prevention of Postoperative Nausea and Vomiting," *Drug Invest* 8(2):67-72 (1994).
Cherry, P.M.H., et al., "The Treatment of Pain Following Excimer Laser Photorefractive Keratectomy: Additive Effect of Local Anesthetic Drops, Topical Diclofenac, and Bandage Soft Contact," *Opthalmic Surg Lasers* 27:S477-S480 (1996).
Gurbaxani, A., et al., "Intracameral phenylephrine to prevent floppy iris syndrome during cataract surgery in patients on tamsulosin," *Eye* 21:331-332 (2007).
Goyal, R., et al., "Randomised Controlled Trial of Ketorolac in the Management of Corneal Abrasions," *Acta Ophthalmol. Scand.* 79:177-179 (2001).
Arshinoff, S., et al., "Use of Topical Nonsteroidal Anti-Inflammatory Drugs in Excimer Laser Photorefractive Keratectomy," *J Cataract Refract Surg* 20:216-222 (1994).
Busse, W., et al., "A Multicenter, Double-Blind, Randomized, Placebo-Controlled Trial Comparing the Efficacy and Tolerability of Levocabastine-Oxymetazoline Nasal Spray with Levocabastine and Oxymetazoline Alone in the Symptomatic Treatment of Seasonal Allergic Rhinitis," *American Journal of Rhinology* 10(2):105-111 (1996).
Quiroz, C., et al., "N.F.12: A New Topical Solution for External Eye Disease," *American Journal of Ophthalmology* 41(6):1020-1024 (1956).
Grahn, B., et al., "Diagnostic Ophthalmology," *Can Vet J* 35:730-731 (1994).

(56) References Cited

OTHER PUBLICATIONS

Angra, S.K., et al., "Safe and Effective Management of Vernal Keratoconjunctivitis (VKC): A Double Blind Clinical Study," *Ann Natl Acad Med Sci (India)* 25(1):9-12 (1989).
Batra, D., et al., "Patterns of Responses to Alternative Medicines in Controlling Allergic Conjunctivitis," *Ind. J. Ophthal* 36(1):17-21 (1988).
Matsuda, M., et al., "The Addition of Oxidized Glutathione to Intraocular Irrigating Solutions to Prevent Corneal Endothelial Damage During Intraocular Surgery," *Folia Ophthalmol Jpn* 41:1093-1098 (1990). Japanese Language (Original).
Matsuda, M., et al., "The Addition of Oxidized Glutathione to Intraocular Irrigating Solutions to Prevent Corneal Endothelial Damage During Intraocular Surgery," *Folia Ophthalmol Jpn* 41:1093-1098 (1990). English translated copy.
Nishide, T., et al., "Topical Anesthesia with Additional Intracameral Irrigation of 0.2% Lidocaine during Cataract Surgery in High Myopic Eyes," *Jpn J Clin Ophthalmol* 53(5):921-922 (1999). Japanese Language (Original).
Nishide, T., et al., "Topical Anesthesia with Additional Intracameral Irrigation of 0.2% Lidocaine during Cataract Surgery in High Myopic Eyes," *Jpn J Clin Ophthalmol* 53(5):921-922 (1999). English translated copy.
Kinoshita, A., "Mydriatic Efficacy of Irrigated Phenylephrine during Extracapsular Cataract Surgery," *Folia Ophthalmol Jpn* 40:1730-1733 (1989). Japanese Language (Original).
Kinoshita, A., "Mydriatic Efficacy of Irrigated Phenylephrine during Extracapsular Cataract Surgery," *Folia Ophthalmol Jpn* 40:1730-1733 (1989). English translated copy.
Tsuchisaka, H., "How to Use Surgical Adjuvents and Drugs in IOL Implantation," *Journal of the Eye* 4(6):755-759 (1987). Japanese Language (Original).
Tsuchisaka, H., "How to Use Surgical Adjuvents and Drugs in IOL Implantation," *Journal of the Eye* 4(6):755-759 (1987). English translated copy.
Lacy, C. et al, "Drug Information Handbook," Lexi-Comp, Inc. Cleveland, Ohio, pp. 497 and 717-719, (1993).
Lundberg, B. et al., "Intracameral Mydriatics in Phacoemulsification Surgery Obviate the Need for Epinephrine Irrigation," *Acta Ophthalmol. Scand.* 85:546-550 (2007).
Katsura, Hiroshi, "How to Use Local Anesthetic," Eye Clinic 27:1055-1060 (1985). Japanese language.
Katsura, Hiroshi, "How to Use Local Anesthetic," Eye Clinic 27:1055-1060 (1985). English translation.
Crandall, A., et al. (Oct. 2011). *OMS302 Maintains Mydriasis and Decrease Postoperative Pain in Cataract Surgery*. Poster Session presented at the meeting of the American Academy of Ophthalmology, Orlando, FL.
Sandoval, H.P., et al., "A review of the use of ketorolac tromethamine 0.4% in the treatment of post-surgical inflammation following cataract and refractive surgery," *Clin Ophthalmol* 1(4):367-71 (2007).
Suleiman, Y.M., et al., "Comparison of ketorolac tromethamine and prednisolone acetate in preventing surgically induced miosis during cataract surgery," *Sultan Qaboos Univ Med J* 10(1):57-63 (2010).
Stewart, R. et al., "Efficacy and Safety Profile of Ketorolac 0.5% Ophthalmic Solution in the Prevention of Surgically Induced Miosis During Cataract Surgery," *Clinical Therapeutics* 21(4):723-732 (1999).
ADRENALIN [package insert]. JPH Pharmaceuticals, LLC, Rochester, MI; 2004.
Arshinoff, S.A., et al. (2009). The pharmacotherapy of cataract surgery. In *Ophthalmology* (M. Yanoff and J.S. Duker, Eds.) Third Edition. (pp. 434-40). Elsevier.
Batenburg, W., et al., "Carvedilol-induced antagonism of angiotensin II: a matter of $\alpha_1$-adrenoceptor blockade," *Journal of Hypertension* 24:1355-1363 (2006).
Behndig, A., et al., "Mydriatic response to different concentrations of intercameral phenylephrine in humans," *J Cataract Refract* 36:1682-1686 (2010).
Bhattacharjee, A.K., et al., "MMP-9 and EBA immunoreactivity after papaverine mediated opening of the blood-brain barrier," *NeuroReport* 13:2217-2221 (2002).
Fine, I.H., et al. (2009). Phacoemulsification in the presence of a small pupil. In *Cataract Surgery: Expert Consult* (R. Steinert, Ed.) Third Edition (pp. 245-258). Elsevier.
Flach, A.J., et al., "Improvement in visual acuity in chronic aphakic and pseudophakic cystoid macular edema after treatment with topical 0.5% ketorolac tromethamine," *Am J Ophthalmol* 112:514-519 (1991).
Guzek, J.P., et al., "Risk factors for intraoperative complications in 1000 extracapsular cataract cases," *Ophthalmology* 94:461-466 (1987).
Ho, T., et al., "Maximal mydriasis evaluation in cataract surgery," *J Cataract Refract Surg* 18:375-379 (1992).
Holló, G. "The side effects of the prostaglandin analogues," *Expert Opin Drug Saf* 6(1):45-52 (2007).
Kozlowska, H., et al., "Ligands at $\beta_2$-, $\beta_3$-, and the low-affinity state of $\beta_1$-adrenoceptors block the $\alpha_1$-adrenoceptor-mediated constriction in human pulmonary and rat mesenteric arteries," *J Cardiovasc Pharmacol* 46(1):76-82 (2005).
Mamalis, N. (2009). Toxic anterior segment syndrome. In *Cataract Surgery: Expert Consult* (R. Steinert, Ed.) Third Edition. (pp. 589-594). Elsevier.
Moroi, S.E., et al. (2001). Ocular pharmacology. In *Goodman & Gilman's The Pharmacological Basis of Therapeutics* (J.G. Hardman and L.E. Limbird, Eds.) Tenth Edition. (pp. 1821-1848). McGraw-Hill.
Nakamura, S., et al., "Evaluation of $\alpha_1$-adrenoceptors in the rabbit iris: pharmacological characterization and expression of mRNA," *Br J Pharmacol* 127:1367-1374 (1999).
Narendran, N., et al., "The cataract national dataset electronic multicenter audit of 55 567 operations: risk stratification for posterior capsule rupture and vitreous loss," *Eye* 23:31-37 (2009).
Neuhann, T.F. et al. (2009). Capsulorrhexis. In *Cataract Surgery: Expert Consult* (R. Steinert, Ed.) Third Edition. (pp. 163-171). Elsevier.
Radi, Z.A., et al., "The pathophysiologic role of cyclooxygenases in the eye," *J Ocular Pharmacol Ther* 24(2):141-151 (2008).
Rutar, T., et al., "Risk factors for intraoperative complications in resident-performed phasoemulsificatin surgery," *Ophthalmology* 116:431-436 (2009).
Schalnus, R. "Topical nonsteroidal anti-inflammatory therapy in ophthalmology," *Ophthalmologica* 217:89-98 (2003).
Waitzman, M.B. "Prostaglandins and the eye," *Metabolic, Pediatric and Systemic Ophthalmology* 6:17-26 (1982).
Menapace, R. (2005). Prevention of posterior capsule opacification. In *Cataract and Refractive Surgery* (T. Kohnen and D. Koch, Eds.) (pp. 101-122). Springer.
ACULAR [package insert]. Allergan, Inc., Irvine, CA; 2004.
Srinivasan, M., et al., "Sodium bicarbonate—an alternative to hyaluronidase in ocular anaesthesia for cataract surgery," *Indian Journal of Ophthalmology* 48(4):285-89 (2000).
Solomon, K.D., et al., "Topical 0.5% ketorolac vs 0.03% flurbiprofen for inhibition of miosis during cataract surgery," *Arch Opthalmol* 115:1119-1122 (1997).
Gills, J.P., "Injectable Prostaglandins Inhibitors Prior to Cataract Surgery," *J Cataract Refract* 13:459-460 (1987).
Yuen, V.H., et al., "Comparison of three modified lidocaine solutions for use in eyelid anesthesia," *Ophthalmic Plastic and Reconsturctie Surgery* 15(2):143-147 (1999).
Krohn, J., et al., "Retrobulbar anesthesia with and without hyaluronidase in extracapsular cataract surgery," *Acta Opthalmologica* 71:791-795 (1993).
Slack, J.W., et al., "A bisulfite-free intraocular epinephrine solution," *Am.J.Ophthalmol.* 110(1):77-82 (1990).
Allergan. (2011). Acuvail® (ketorolac tromethamine ophthalmic solution) 0.45%. Irvine, CA. (Package Insert).
Allergan. (2011). Acular—ketorolac tromethamine solution/drops. Irvine, CA. (Package Insert).
Allergan. (2001). Acular® (ketorolac tromethamine ophthalmic solution) 0.5% Sterile. Irvine, CA. (Package Insert).

(56) References Cited

OTHER PUBLICATIONS

Bedford Laboratories. (2008) Ketorolac Tromethamine (ketorolac tromethamine) Injection, Solution. Retrieved from http://dailymed.nlm.nih.gov/dailymed/archives/fdaDrugInfo.cfm?archivedid=8730. (Package Insert).

Falcon Pharmaceuticals, Ltd., et al.(2004) Phenylephrine Hydrochloride Ophthalmic Solution, 2.5%. Fort Worth, TX. (Package Insert).

Phenylephrine Hydrochloride. (2012). In Medicines Support Unit for Optometrists. Retrieved from http://www.med-support.org.uk/IntegratedCRD.nsf/b73d388be6b449968025768c005313. (Package Insert).

InterMed Medical Ltd. (2005). Neo-Synephrine® Phenylephrine Hydrochloride 1% Injection. In Information for Helath Professionals Data Sheet. Retreived from file:////H|/OMS302/Commercial PE and KT products/Neo-Synephrine product info.htm.

Hirowatari, T., et a., "Availability of TPD ophthalmic Solution (Mixture of Mydria-P Solution, Neosynesin Kowa Solution, and Diclod Solution)," New Ophthalmology 19(1):107-109 (2002). Japanese Language.

Hirowatari, T., et a., "Availability of TPD ophthalmic Solution (Mixture of Mydria-P Solution, Neosynesin Kowa Solution, and Diclod Solution)," New Ophthalmology 19(1):107-109 (2002). English Translation.

Ogawa, T., et al., "Effects of Pre-installed Mydriatics on the Intraocular Concentration and Wnti-inflammatory Action of Topical 0.1% Pranoprofen (3)—Study on Permeability Factor," Journal of Japanese Ophthalmological Society 96(11):1379-1386 (1992). Japanese Language.

Ogawa, T., et al., "Effects of Pre-installed Mydriatics on the Intraocular Concentration and Wnti-inflammatory Action of Topical 0.1% Pranoprofen (3)—Study on Permeability Factor," Journal of Japanese Ophthalmological Society 96(11):1379-1386 (1992). English Translation.

Kim, S.J., et al., "Nonsteroidal anti-inflammatory drugs in ophthalmology," Surv. Ophthalmol. 55(2):108-133 (2010).

Lindstrom, R.L., et al., "Intracameral phenylephrine and ketorolac injection (OMS302) for maintenance of intraoperative pupil diameter and reduction of postoperative pain in intraocular lens replacement with phacoemulsification," Clin.Ophthalmol. 8:1735-1744 (2014).

DeRuiter, Principals of Drug Action 2 at 4 (Fall, 2002), accessed Apr. 26, 2015 at www.auburn.edu/~deruija/nsaids_2002.pdf.

Goodman & Gilman's, The Pharmacologic Basis of Therapeutics, 10th edition, pp. 145-6, 216-8, 687-92 (2001).

Hardman, J.G., Ed., *Goodman and Gilman's The Pharmacologic Basis of Therapeutics*, 10$^{th}$ Edition; New York: McGraw-Hill Medical, 2001; pp. 145-6, 216-8, 687-92.

Ansari, H.R., et al., "Effects of prostaglandin F2alpha, latanoprost and carbachol on phosphoinositide turnover, MAP kinases, myosin light chain phosphorylation and contraction and functional existence and expression of FP receptors in bovine iris sphincter," Exp. Eye Res. 78(2):285-296 (2004).

Zanetti, F.R., "Effect of preoperative use of topical prednisolone acetate, ketorolac tromethamine, nepafenac and placebo, on the maintenance of intraoperative mydriasis during cataract surgery: a randomized trial," Indian J. Ophthalmol. 60(4):277-281 (2012).

Zanetti, F.R., et al., "Effect of preoperative use of topical prednisolone acetate, ketorolac tromethamine, nepafenac and placebo, on the maintenance of intraoperative mydriasis during cataract surgery: a randomized trial," *Indian J Ophthalmol*. 60(4):277-81 (2012).

Keulen-de Vos, H.C., et al., "Effect of indomethacin in preventing surgically induced miosis," Br. J. Ophthalmol. 67(2):94-96 (1983).

Guzinska, M., et al.., "[the effect of diclofenac sodium and indomethacin used locally for maintenance of pupillary dilatation during cataract surgery]," Klin.Oczna 100(1):19-22 (1998). English Language Abstract Included.

Guimaraes-Filho,S.R., et al., "Comparison of the anti-inflammatory effects of topically applied aspirin and indomethacin following photocoagulation of the rabbit iris," Braz.J.Med.Biol.Res. 25(1):67-73 (1992).

Ahlquist, RP, "Present State of Alpha- and Beta-Adrenergic Drugs I. The Adrenergic Receptor," Am Heart J. 92(5):661-4 (1976).

Gupta, V.P., et al., "Ketorolac tromethamine in the maintenance of intraoperative mydriasis," Ophthalmic Surg.Lasers 28(9):731-738 (1997).

Cutler Peck, C.M., et al., "Toxic anterior segment syndrome: Common causes," *J Cataract Refract Surg* 36:1073-1080 (2010).

Gills, James, "Cataract Surgery Pharmacology—A leading surgeon shares several ways he's improved his medication protocol and raised his standard of care," Opthalmology Management, Sep. 2001. http://www.ophthalmologymanagement.com/articleviewer.aspx?articleid=85211.

Keates, R.H., et al., "Clinical trial of flurbiprofen to maintain pupillary dilation during cataract surgery," Ann.Ophthalmol. 16(10):919-921 (1984).

Gills, J.P., et al. "Pharmacodynamics of Cataract Surgery" & "Strategies for Applying State of the Art Techniques," Cataract Surgery The State of the Art Chapters 3 & 18:19-26, 229-240 (1998).

Keates, R.H., et al., "The effect of topical indomethacin ophthalmic solution in maintaining mydriasis during cataract surgery," Ann. Ophthalmol. 16(12)1116-1121 (1984).

DeMarinis, Robert, M., et al., (1987) "Structure-Activity Relationships for alpha-1 Adrenergic Receptior Agonists and Antagonists," *The alpha-1 Adrenergic Receptors*, Chapter 6, pp. 211-265.

U.S. National Institutes of Health, "Safety, Efficacy and Pharmacokinectics of OMS302 in Subjects Undergoing Intraocular Lens Replacement With Phacoemulsification," Clinical Trials Identifier: NCT01579565, May 1, 2012, Accessed at https://clinicaltrials.gov/archive/NCT01579565/2012_05_01.

Timmerman, Luke, "Omeros Combo Drug Passes Cataract Surgery Study," Mar. 23, 2011, Accessed at http://www.xconomy.com/seattle/2011/03/23/omeros-combo-drug-passes-cataract-surgery-study/.

Omeros Corporation, "Omeros' Ophthalmology Product OMS302 Achieves Co-Primary Endpoints in Phase 2b Clinical Study—OMS302 Maintains Pupil Dilation During Cataract Surgery and Reduces Postoperative Pain," Mar. 23, 2011, Accessed at http://investor.omeros.com/phoenix.zhtml?c=219263&p=irol-newsArticle_Print&ID=1541955.

Lowry, Fran, "New Drug Maintains Mydriasis During Lens Replacement," Oct. 28, 2011, Accessed at http://medscape.com/viewarticle/752489.

PR Newswire, "Omeros' Ophthalmology Product OMS302 Achieves Primary and Secondary Endpoint in Phase 3 Clinical Trial," Omeros Corporation Press Release, Mar. 13, 2012, Accessed at http://www.virtualizationconference.com/node/2202855.

Rosenblatt, Mark, et al., "A Phase 3 clinical trial of the drug product OMS302 delivered intracamerally in BSS during intraocular lens replacement surgery," American Academy of Ophthalmology Annual Meeting, Nov. 10, 2012 (Conference Poster).

PR Newswire, "Omeros to Present Data from Successful OMS302 Phase 3 Clinical Trial at the American Academy of Ophthalmology Annual Meeting," Omeros Corporation Press Release, Nov. 8, 2012, Accessed at http://www.prnewswire.com/news-releases/omeros-to-present-data-from-successful-oms302-phase-3-clinical-trial-at-the-american-academy-of-ophthalmology-annual-meeting-177836051.html.

PR Newswire, "Omeros Announces Positive OMS302 Safety Data in Phase 3 Clinical Trial," Omeros Corporation Press Release, Jan. 22, 2013, Accessed at http://www.prnewswire.com/news-releases/omeros-announces-positive-oms302-safety-data-in-phase-3-clinical-trial-187854311.html.

U.S. National Institutes of Health, "Safety and Efficacy of OMS302 in Subjects Undergoing Intraocular Lens Replacement With Phacoemulsification," Clinical Trials Identifier: NCT01454063, May 1, 2012, Accessed at https://clinicaltrials.gov/archive/NCT01454063/2012_05_01.

(56) References Cited

OTHER PUBLICATIONS

A.D.A.M., Inc., "Cataracts In-depth report," *The New York Times*, 2008, Accessed at http://www.nytimes.com/health/guides/disease/cataract/print.html, Accessed on Jan. 22, 2016.
Al-Ghouri, A.R., M.D., "Toxic Anterior Segment Syndrome," Sep. 9, 2014 Accessed at http://emedicine.medscape.com/article/1190343-overview, Accessed on Jan. 22, 2016.
Artzen, D., et al., "Capsule complication during cataract surgery: Case-control study of preoperative and intraoperative risk factors: Swedish Capsule Rupture Study Group report 2," *J Cataract Refract Surg* 35(10):1688-1693 (2009)
Behndig, A., et al., "Intracameral mydriatics in cataract surgery," *Cataract Surgery*, Zaidi F. (ed.), Rijeka, Croatia: InTech 2013:149-172.
Biswas, P.S., et al, "Role of Inflammatory Cytokine-induced Cyclooxygenase 2 in the Ocular Immunopathologic Disease Herpetic Stromal Keratitis," *J Virol* 79(16):10589-600 (2005).
Bucci, F.A., Jr., et al., "Prostaglandin E2 Inhibition of Ketorolac 0.45%, Bromfenac 0.09%, and Nepafenac 0.1% in Patients Undergoing Phacoemulsification," *Adv Ther* 28(12):1089-95 (2011).
Cervantes-Coste, G., et al., "Inhibition of surgically induced miosis and prevention of postoperative macular edema with nepafenac," *Clin Ophthalmol* 3:219-226(2009).
Chang, D.F., Campbell, J.R., "Intraoperative floppy iris syndrome associated with tamsulosin," *J Cataract Refract Surg* 31(4):664-673.22 (2005).
Chang, D.F., et al., "Prospective multicenter evaluation of cataract surgery in patients taking tamsulosin (Flomax)" *Ophthalmology* 114(5):957-964 (2007).
Pandya, Hemang K., "Postoperative Endophthalmitis Treatment & Management," Updated Jan. 5, 2016, Accessed at http://emedicine.medscape.com/article/1201260-treatment, Accessed on Jan. 25, 2016.
Caronia, R.M., "Antiinflammatory Effect of Preoperative Ketorolac in Phacoemulsification," *J Cataract Refract Surg.* 28(10):1880-1 (2002).
Cohen, S., et al., "Cystoid macular edema after pars plana vitrectomy for retained lens fragments," *J Cataract Surg* 32:1521-1526 (2006).
Colin, J., "The Role of NSAIDs in the Management of Postoperative Ophthalmic Inflammation," *Drugs* 67(9):1291-308 (2007).
Davis, J.L., et al., "Sustained-release Celecoxib From Incubated Acrylic Intraocular Lenses Suppresses Lens Epithelial Cell Growth in an Ex Vivo Model of Posterior Capsule Opacity," *J Ocul Pharmacol Ther.* 28(4):359-68 (2012).
Donnenfeld, E.D., et al., "Preoperative Ketorolac Tromethamine 0.4% in Phacoemulsification Outcomes: Pharmacokinetic-response Curve," *J Cataract_Refract Surg.* 32(9):1474-82 (2006).
Flach, A., "The incidence, pathogenesis and treatment of cystoid macular edema following cataract surgery," *Trans Am Ophthalmol Soc* 96:557-634 (1998).
Graff, G. et al., "Transient loss of prostaglandin synthetic capacity in rabbit iris-ciliary body following anterior chamber paracentesis," *Ocular Immunology and Inflammation* 6(4):227-238 (1998).
Greenberg, P.B., et al., "Prevalence and predictors of ocular complications associated with cataract surgery in United States veterans," *Ophthalmology* 118(3):507-514 (2011).
Haridas, A,, et al., "Intraoperative floppy iris syndrome (IFIS) in patients receiving tamsulosin or doxazosin-a UK-based comparison of incidence and complication rates" *Graefes Arch Clin Exp Ophthalmol* 251(6):1541-1545 (2013).
Henderson, B., et al., "Clinical pseudophakic cystoid macular edema. Risk factors for development and duration of treatment," *J Cataract Refract Surg* 33:1550-1558 (2007).
Iliff, W., "Aphakic cystoid macular edema and the operating microscope: is there a connection?" *Trans Am Ophthalmol Soc* 83:476-500(1985).
Ismail, R., Sallam, A., "Complications associated with cataract surgery," *Cataract Surgery*, Zaidi F. (ed.), Rijeka, Croatia: InTech 2013:221-244.

Knobbe, C.A., M.D., "Cataract Surgery Complications," 2016, Accessed at http://www.allaboutvision.com/conditions/cataract-complications.htm Accessed on Jan. 25, 2016.
Lobo, C., "Pseudophakic cystoid macular edema," *Ophthalmologica* 227(2):61-67 (2012).
Loewenstein, A., Zur, D., "Postsurgical Cystoid Macular Edema," *Macular Edema, Dev Ophthalmol.*, Coscas, G. (ed.), Basel, Karger 2010:148-159.
McCarey, B.E., et al., "Corneal Wound Healing Strength with Topical Antiinflammatory Drugs," *Cornea* 14(3):290-4 (1995).
Oetting, T., "Complicated cataract cases. Cataract surgery and diabetes," *ASCRS EyeWorld*, Nov. 2012, Accessed at http://www.eyeworld.org/article-cataract-surgery-and-diabetes, Accessed on Jan. 25, 2016.
Ostri C., et al., "Phacoemulsification cataract surgery in a large cohort of diabetes patients: visual acuity outcomes and prognostic factors," *J Cataract Refract Surg* 37(11):2006-2012 (2011).
Patalano, V.J., "The risks and benefits of cataract surgery," *Digital Journal of Ophthalmology*, Oct. 15, 2002, Accessed at http://www.djo.harvard.edu/site.php?url=/patients/pi/408, Accessed on Jan. 22, 2016.
Reddy, A.C., M.D, "Diagnosis and Management of Choroidal Effusions," *Ophthalmic Pearls—Glaucoma—Eyenet*, Nov. 2012, 47-49, Accessed at http://www.aao.org/publications/eyenet/201211/pearls.cfm?RenderForPrint=1&.
Rogue, M.R., M.D., M.B.A., F.P.A.O, "Vitreous Wick Syndrome.," 2011, Accessed at http://emedicine.medscape.com/article/1230457-overview#a0101, Accessed on Jan. 25, 2016.
Roth, D.B., M.D., "Nonpseudophakic Cystoid Macular Edema," Apr. 21, 2014, Accessed at http://emedicine.medscape.com/article/1225735-overview#showall, Accessed on Jan. 22, 2016.
Rowen, S., "Preoperative and Postoperative Medications Used for Cataract Surgery," *Curr Opin Ophthalmol.* 10(1):29-35 (1999).
Scott, J.A., et al., "Surgically Induced Diffuse Scleritis Following Cataract Surgery," *Eye* (*Lond*). 8 (Pt 3):292-7 (1994).
Wielders, L., et al., "Prevention of CME after cataract surgery," *Cataract Refract Surg Today Eur.* 53-55 (2013).
Wikipedia contributors, "Synechia (eye)," *Wikipedia, The Free Encyclopedia*, Last Updated Feb. 2, 2015, Accessed at http://en.wikipedia.org/wiki/Synechia_(eye), Accessed on Jan. 25, 2016.
Wolf, E.J., et al., "Incidence of visually significant pseudophakic macular edema after uneventful phacoemulsification in patients treated with nepafenac," *J Cataract Refract Surg* 33:1546-1549 (2007).
Zare, M., et al., "Risk factors for posterior capsule rupture and vitreous loss during phacoemulsification," *J Ophthalmic Vis Res.* 4(4):208-212 (2009).
Kim, Y.Y., et al., "Biphasic Intraocular Pressure Response to Laser Irradiation of the Iris in Rabbits," *Ophthalmic Res* 27(4):243-8 (1995).
Miyake, K., Ibaraki, N., "Prostaglandins and cystoid macular edema" *Surv Ophthalmol* 2(47 suppl 1):S203-518 (2002).
Rossetti, L., Autelitano, A., "Cystoid macular edema following cataract surgery," *Opin Ophthalmol* 11:65-72 (2000).
Shimura, M., et al., "Panretinal photocoagulation induces proinflammatory cytokines and macular thickening in high-risk proliferative diabetic retinopathy," *Graefes Arch Clin Exp Ophthalmol* 11:65-72 (2000).
Olson, N.Y., et al., "Nonsteroidal anti-inflammatory drug therapy in chronic childhood iridocyclitis," *Am J Dis Child* 142(12):1289-92 (1988).
Kotaniemi, K., et al., "Intraocular Lens Implantation in Patients with Juvenile Idiopathic Arthritis-Associated Uveitis," *Ophthalmic Res.* 38(6):318-23 (2006).
Behera, U.C., "Epiretinal Deposits Post Cataract Extraction," *Retin Cases Brief Rep.* 7(4):359-61 (2013).
Iwase, T., "Reiterative Membranous Proliferation With Giant-Cell Deposits on Hydrophobic Acrylic Intraocular Lenses After Triple Procedures in Eyes with Cataracts and Uveitis," *Cutan Ocul Toxicol.* 29(4):306-11 (2010).
Ness, T., et al., "Toxic Vitreitis Outbreak After Intravitreal Injection," *Retina.* 30(2):332-8 (2010).

(56) References Cited

OTHER PUBLICATIONS

Matsuo, K., et al., "Clinical Efficacy of Diclofenac Sodium on Postsurgical Inflammation After Intraocular Lens Implantation," *Refract Surg*. 21(3):309-12 (1995).
Banker, A.S., "Vision-Threatening Complications of Surgery for Full-Thickness Macular Holes. Vitrectomy for Macular Hole Study Group," *Ophthalmology*. 104(9):1442-52 (1997).
Russo, A., et al., "A Randomised Controlled Trial of Ranibizumab With and Without Ketorolac Eyedrops for Exudative Age-Related Macular Degeneration," *Br J Ophthalmol*. 97(10):1273-6 (2013).
Warwar, R., et al., "Cystoid macular edema and anterior uveitis associated with latanoprost use. Experience and incidence in a retrospective review of 94 patients," *Ophthalmology* 105:263-268 (1998).
Obstbaum, S.A., et al., "Cystoid macular oedema and ocular inflammation. The corneo-retinal inflammatory syndrome," *Trans.Ophthalmol. Soc.U.K.* 99(1):187-191 (1979).
Kreiger, A., et al., "Incisional Complications in Pars plana Vitrectomy," *Mod.Probl.Ophthal*. 18:210-223 (1977).
Balyeat, H.D., et al., "Nylon suture toxicity after cataract surgery," *Ophthalmology* 95(11):1509-1514 (1988).
Hiraoka, M., et al., "Factors contributing to corneal complications after vitrectomy in diabetic patients," *Jpn.J.Ophthalmol*. 45(5):492-495 (2001).
Schmier, J.K., et al., "Evaluation of costs for cystoid macular edema among patients after cataract surgery," *Retina* 27(5):621-628 (2007).
National Diabetes Clearing House, "*Diabetes A-Z—National Institute of Diabetes and Digestive and Kidney Disease,*" 2016, Accessed at diabetes.niddk.nih.gov, Accessed on Jan. 26, 2016.
Florio, V., et al., "Ocular Tissue Distribution of Ketorolac After Administration of OMS302 to Dogs During IOL Replacement," *American Society of Cataract and Refractive Surgery Conference*, San Diego, CA, Apr. 17, 2015 (Conference Abstract).
Florio, V., et al., "Ocular Tissue Distribution of Ketorolac After Administration of OMS302 to Dogs During IOL Replacement," *American Society of Cataract and Refractive Surgery Conference*, San Diego, CA, Apr. 17, 2015 (Conference Poster).
Katsev, D., et al. "Intercameral Ketorolac Concentration Following Topical Ketorolac Administration Prior to Cataract Surgery," *American Society of Cataract and Refractive Surgery Conference*, San Diego, CA, Apr. 17, 2015 (Conference Abstract).
Katsev, D., et al. "Intercameral Ketorolac Concentration Following Topical Ketorolac Administration Prior to Cataract Surgery," *American Society of Cataract and Refractive Surgery Conference*, San Diego, CA, Apr. 17, 2015 (Conference Poster).
Donnefeld, E., et al., "OMS302 in Patients with Diabetes Mellitus," *American Academy of Ophthamology Annual Meeting*, Chicago, IL, Oct. 18, 2014 (Conference Poster).
McDermott, M.L., et al., "Ophthalmic irrigants: a current review and update," *Ophthalmic Surg*.19(10):724-733 (1988).
Haimann, M.H.., et al., "Prophylactic timolol for the prevention of high intraocular pressure after cataract extraction. A randomized, prospective, double-blind trial," *Ophthalmology* 88(3):233-238 (1981).
Crandall, A.S., et al., "A comparison of patient comfort during cataract surgery with topical anesthesia versus topical anesthesia and intracameral lidocaine," *Ophthalmology* 106(1):60-66 (1999).
Duffin, R.M., et al., "2.5% v 10% phenylephrine in maintaining mydriasis during cataract surgery," *Arch.Ophthalmol*. 101(12):1903-1906 (1983).
Stewart, R., et al., "Efficacy and safety profile of ketorolac 0.5% ophthalmic solution in the prevention of surgically induced miosis during cataract surgery," *Clin.Ther*. 21(4):723-732 (1999).
Lundberg, B., et al., "Intracameral mydriatics in phacoemulsification cataract surgery," *J Cataract Refract Surg* 29:2366-2371 (2003).
Bandyopadhyay, P., et al. (2010). Development of ophthalmic formulation. In *Pharmaceutical Dosage Forms* (pp. 254-286) New York:NY: Informa Healthcare.
Brown, M.R.W., et al., "The Preservation of Ophthalmic Preparations," *J. Soc. Cosmetic Chemists* 16:369-393 (1965).

Das Gupta, V., et al., "Chemical Stabilities of Lignocaine Hydrochloride and Phenylephrine Hydrochloride in Aqueous Solution," *Journal of Clinical and Hospital Pharmacy* 11:449-452 (1986).
Edelhauser, H.F., et al., "Corneal Edema and the Intraocular Use of Epinephrine," *American Journal of Ophthalomology* 93:327-333 (1982).
Ellis, P.P. (1981). Basic considerations. In *Ocular Therapeutics and Pharmacology* (pp. 3-23) St. Louis:MO:The C.V. Mosby Company.
Food and Drug Administration, "Guidance for Industry Q1A(R2) Stability Testing of New Drugs Substances and Products," (2003).
Heath, P., et al., "Use of Phenylephrine Hydrochloride (Neo-Synephrine Hydrochloride®) in Ophthalmology," *Archives of Ophthalmology* 41(2):172-177 (1949).
Lang, J.C., et al. (2002). Design and Evalution of Ophthalmic Pharmaceutical Products. In *Modern Pharmaceutics* (pp. 626-698) Fort Worth:TX:Marcel Decker, Inc.
Lewis, R.J. (2007). *Hawley's Condensed Chemical Dictionary*, $15^{th}$ Edition, (pp. 188-189), Hoboken:NJ: John Wiley & Sons, Inc.
Mauger, T.F., et al. (1996). *Mosby's Ocular Drug Handbook* (pp. 36-40), St. Louis:MO: Mosby-Year Book, Inc.
Öztürk, F., et al., "The efficacy of 2.5% phenylephrine and flurbiprofen combined in inducing and maintaing pupillary dilatation during cataract surgery," *European Journal of Ophthalmology* 10(2):144-148 (2000).
*Physicians' Desk Reference for Ophthamology*, $26^{th}$ Edition, (pp. 1-2, 7-8, 15, 201, 209, 221-222, 235) (1998).
*Physicians' Desk Reference for Nonprescription Drugs and Dietary Supplements*, $24^{th}$ Edition, (pp. 620-621) (2003).
Reddy, I.K. (Ed.), (1996). *Ocular Therapeutics and Drug Delivery*, (pp. 3-29, 171-193, 204, 377-404, 529-540.
Lang, J.C., et al., (2005). Ophthalmic Preparations. In *Remington—The Science and Practice of Pharmacy*.$21^{st}$ Edition, (pp. 850-870).
*The United States Pharmacopeia*, $23^{rd}$ Edition, (pp. 10-14, 1211-1217, 1940-1947, 1959-1963) (1995).
Brandl, M., et al., "Approaches for Improving the Stability of Ketorolac in Powder Blends," *Journal of Pharmaceutical Sciences* 84(10):1151-1153 (1995).
Brandl, M., et al., "Racemization of Ketorolac in Aqueous Solution," *Journal of Pharmaceutical Sciences* 84(9):1045-1048 (1995).
Center for Drug Evaluation and Research, "Application No. 21-132 Chemistry Review(s)," 2009.
Center for Drug Evaluation and Research, "Application No. 207926Orig1s000 Chemistry Review(s)," 2014.
Center for Drug Evaluation and Research, "Application No. 207926Orig1s000 Summary Review," 2015.
Das Gupta, V., et al., "Stability of Phenylephrine Hydrochloride Nasal Drops," *American Journal of Hospital Pharmacy* 29:870-873 (1972).
Gu, L., et al., "Kinetics and mechanisms of the autoxidation of ketorolac tromethamine in aqueous solution," *International Journal of Pharmaceutics* 41:95-104 (1988).
Gu, L., et al., "Light degradation of ketorolac tromethamine." *International Journal of Pharmaceutics* 41:105-113 (1988).
Millard, B.J., et al., "The stability of aqueous solutions of phenylephrine at elevated temperatures: identification of the decomposition products," *J. Pharm. Pharmac*. 25(Suppl.):24p-31p (1973).
NEO-SYNEPHRINE—phenylephrine hydrochloride injection, solution [Package Insert]. Lake Forest, IL:Hospira, Inc., 2010.
PHENYLEPHRINE 10MG/ML Solution for Injection of Infusion [Package Insert] Kent, UK: Beacon Pharmaceuticals (2011).
Omeros Corporation, Response to Communication Pursuant to Article 94(3), European Patent Application No. 03 772122.2. Sep. 15, 2011.
Code of Federal Regulation, 21 CFR Subchapter C:Drugs: General: Part 200-General, (pp. 5-8). Updated Apr. 1, 2015.
ACULAR® (ketorolac tromethamine ophthalmic solution) 0.5% [Package Insert]. Irvine, CA: Allergan, Inc.; 2001.
ACULAR® PF (ketorolac tromethamine ophthalmic solution) 0.5% Preservative-Free [Package Insert]. Irvine, CA: Allergan, Inc.; 2002.
ACUVAIL™ (ketorolac tromethamine ophthalmic solution) 0.45% [Package Insert]. Irvine, CA: Allergan, Inc.; 2009.
BSS Plus® Sterile Intraocular Irrigating Solution [Package Insert]. Fort Worth, TX: Alcon Labatories, Inc., 2003.

(56) References Cited

OTHER PUBLICATIONS

OCUFEN® (flurbiprofen sodium ophthalmic solution, USP) 0.03% [Package Insert]. Irvine,CA: Allergan, Inc., 2001.
Phenylephrine Hydrochoride Ophthalmic Solution, USP 2.5%-Sterile [Package Insert]. Lake Forset, IL: Akorn, Inc., 2011.
*Physicians' Desk Reference*, 50$^{th}$ Edition, (pp. 2325-2326) (1996).
Adamczyk, D.T.; Jaanus, S.D., Antiallergy Drugs and Decongestants. In *Clinical Ocular Pharmacology*; Bartlett, J.D., Ed.; 5$^{th}$ Edition; Butterworth, Heinemann, Elsevier: St. Louis, 2008; pp. 247.
Belmonte C., et al., "Neural basis of sensation in intact and injured corneas," *Exp Eye Res*. 78(3):513-25 (2004).
Coman, O.A., et al., Particularities of vascular reactivity of the conjunctiva and iris in rats, *Romanian journal of morphology and embryology = Revue roumaine de morphologic et embryologie* 49(1):53-56 (2008).
Floman, N., et al., "Mechanism of steroid action in ocular inflammation: Inhibition of prostaglandin production,"*Invest Ophthalmol Vis Sci.* 16(1):69-73 (1977).
Grosser, T. et al., Anti-Inflammatory, Antipyretic, and Analgesic Agents; Pharmacotherapy of Gout. In *Goodman and Gilman's Pharmacological Basis of Therapeutics*, 12$^{th}$ Edition; Brunton, L., Ed.; New York: Mc Graw Hill Medical, 2011; pp. 962-963.
Hashimoto, Y., et al., "Effects of ciliary ganglionectomy on contractile responses in the dilator muscle of the rat iris," *Exp Eye Res*. 56(2):135-41 (1993).
Hoffman, B., Catecholamine, Sympathomimetic Drugs, and Adrenergic Receptor Antagonists. In *Goodman and Gilman's Pharmacological Basis of Therapeutics*, 10$^{th}$ Edition. Hardman, J.G., Ed.; New York: McGraw Hill Medical, 2001, pp. 232.
Loux J, Yankell S. Ocular vasocongestion assay in rabbits. Federation Proceedings 1973 32:3(I).
Miyake, K., et al., "Prevention of cystoid macular edema after lens extraction by topical indomethacin. III. Radioimmunoassay measurements of prostaglandins in the aqueous during and after lens extraction procedures," *Graefes Arch Clin Exp Ophthalmol* 209: 83-88, (1978).
Novack, G.D., "Ophthalmic drug development: procedural considerations," *J Glaucoma* 7(3):202-9 (1998).
Perkins, E.S., "Prostaglandins and ocular trauma," *Adv Ophthalmol*. 34:149-52 (1977).
Portello, J.K. Mydriatics and Mydriolytics. In *Clinical Ocular Pharmacology*; Bartlett, J.D., Ed.; St. Louis: Butterworth, Heinemann, Elsevier, 2008; pp. 114, 117.
Rao, K.N., et al., "Role of aspirin in cataract surgery," *Indian J Ophthalmol*. 33(2):89-90 (1985).
Toris, C.B., et al., "The biology, pathology and therapeutic use of prostaglandins in the eye," *Clinical Lipidology* 6(5):577-591 (2011).
Zschauer, A., et al., "Role of endothelium and hyperpolarization in CGRP-induced vasodilation of rabbit ophthalmic artery," *American Journal of Physiology—Heart and Circulatory Physiology* 263(2):32-2(H359-H365) (1992).
Gamache, D.A., et al., "Nepafenac, a unique nonsteroidal prodrug with potential utility in the treatment of trauma-induced ocular inflammation: I. Assessment of anti-inflammatory efficacy" *Inflammation* 24(4):357-70 (2000).
Whitaker, JS, Declaration under 37 CFR 1.132 dated Feb. 14, 2012.
Omeros Corporation, "Safety, Efficacy and Pharmacokinetics of OMS302 in Subjects Undergoing Intraocular Lens Replacements With Phacoemulsification," *Smart Patients, Inc*. (2016).
U.S. National Institutes of Health, Safety, "Efficacy and Pharmacokinetics of OMS302 in Subjects Undergoing Intraocular Lens Replacement With Phacoemulsification," Clinical Trials Identifier NCT0157956, Oct. 10, 2012, Accessed at http://clinical-trials.gov/archive/NCT01579565/2012_10_10.
Sandoz, Inc., "TROPICAMIDE—tropicamide solution/drops," Drug Label. Updated Jan. 5, 2016. Accessed at https://dailymed.nlm.nih.gov/dailymed/drugInfo.cfm?setid=521592d1-53a1-4314-8b3f-d808f3bccfcd.
Yoshitomi, T., et al. "Functional innervation and contractile properties of the human iris sphincter muscle," *Exp.Eye Res*. 46(6):979-986 (1988).
Yoshitomi, T., et al., "Adrenergic excitatory and cholinergic inhibitory innervations in the human iris dilator," *Exp.Eye Res*. 40(3):453-459 (1985).
Osher, R.H., et al., "OMS302 (phenylephrine and ketorolac injection) 1%/0.3% to maintain intraoperative pupil size and to prevent postoperative ocular pain in cataract surgery with intraocular lens replacement," *Expert Rev. Ophthalmol*. 10(2):91-103 (2015).
Kumar, V., et al., "Systemic Absorption and Cardiovascular Effects of Phenylephrine Eyedrops," *American Journal of Ophthalmology* 99(2):180-184 (1985).
Roberts, C.W., "Comparison of diclofenac sodium and flurbiprofen for inhibition of surgically induced miosis," *J Cataract Refract Surg* 22(Supplement):780-787 (1996).
U.S. National Institute of Health, "Safety and Efficacy of OMS302 in Subjects Undergoing Intraocular Lens Replacement With Phacoemulsification (OMS302-ILR-003)," Clinical Trials Identifier: NCT01454063, Oct. 13, 2011. Accessed at https://clinicaltrials.gov/ct2/show/study/NCT01454063?view=record.
Food & Drug Administration, "Drug Standards Manual," Jan. 5, 2017. Accessed at http://www.fda.gov/Drugs/DevelopmentApprovalProcess/FormsSubmissionRequirements/ElectronicSubmission/DataStandards.
Murrill, C. A., et al., "Optometric Clinical Practice Guideline—Care of The Adult Patient with Cataract—Reference Guide for Clinicians," *American Optometric Association* 43 pages, (2010).
Grob, S. R., et al., "Management of mydriasis and pain in cataract and intraocular lens surgery: review of current medications and future directions." *Clin Ophthalmol* 8:1281-1289 (2014).
Burling-Phillips, L. "After Cataract Surgery: Watching for Cystoid Macular Edema." *EyeNet Magazine* 1-6 (Jan. 2007).
Newton, D. W., "Drug incompatibility chemistry," *Am J Health Syst Pharm* 66(4):348-357 (2009).
Newton, D. W., "Physicochemical Determinants of Incompatibility and Instability of Drugs for Injection and Infusion," In: *Handbook on Injectable Drugs (3rd Edition)*,Ed. L. A. Trissel, 3rd Edition ed., American Society of Hospital Pharmacists' Special Projects Division, (1983).
Troup, A. E., et al., "Degradation of Phenylephrine Hydrochloride in Tablet Formulations Containing Aspirin," *J Pharm Sci* 53:375-379 (1964).
Chusa zai, Injection agent—The knowledge, basics and application thereof-), NANZANDO Co., Ltd., Mar. 22, 1995, First edition, p. 19-20.

\* cited by examiner

ANTI-INFLAMMATORY AND MYDRIATIC INTRACAMERAL SOLUTIONS FOR INHIBITION OF POSTOPERATIVE OCULAR INFLAMMATORY CONDITIONS

CROSS REFERENCE TO RELATED APPLICATION

The present application is a continuation of U.S. patent application Ser. No. 15/836,772, filed Dec. 8, 2017, which is continuation of prior U.S. patent application Ser. No. 14/953,806, filed Nov. 30, 2015, now abandoned, which claims the benefit of U.S. Provisional Application No. 62/086,133 filed Dec. 1, 2014, priority from the filing dates of which are hereby claimed under 35 U.S.C. § 120.

I. FIELD OF THE INVENTION

The present invention relates to methods of using liquid pharmaceutical compositions including a nonsteroidal anti-inflammatory agent and an alpha-adrenergic mydriatic agent for intraocular administration during an ophthalmologic surgical procedure to inhibit postoperative inflammatory conditions.

II. BACKGROUND OF THE INVENTION

Ophthalmologic surgery necessarily results in trauma to delicate intraocular structures that induces prostaglandin synthesis and the inflammatory cascade. The resulting inflammation can result in the occurrence of excess inflammation and associated postoperative inflammatory conditions, particularly in subjects having a preoperative condition placing them at elevated risk for postoperative inflammatory conditions or that may experience an elevated level of surgical trauma.

Ocular surgery often requires the use of a physiologic irrigation solution to facilitate the procedure and to protect and maintain the physiological integrity of intraocular tissues. Examples of ophthalmologic surgical procedures typically requiring irrigation solutions include cataract extraction and lens replacement and refractive lens exchange procedures, corneal transplant procedures and vitreoretinal operations and trabeculectomy procedures for glaucoma. Throughout the intraocular surgery, a patient's pupil must be sufficiently dilated to permit a clear operative field and to limit the trauma that can be associated with the procedure. Pupil dilation (mydriasis) is typically achieved by dilating the eye preoperatively by topical administration of a mydriatic agent.

During the surgery, as the tips of surgical tools are inserted into the anterior chamber of the eye and surgical trauma is induced, the iris sphincter muscle tends to constrict (miosis), reducing the window defined by the pupil. If pupil diameter is not maintained adequately throughout the procedure, the risk of injuring structures within the eye increases and the required operating time is often prolonged. Clinically significant reductions in pupil diameter are associated with an increase in procedure-related complications, including posterior capsule tears, retained lens fragments and vitreous leaks.

Many ophthalmologic surgeons may incorporate epinephrine into the intraocular irrigation solution to assist in the maintenance of pupil dilation. While epinephrine is a alpha- and beta-adrenergic agonist, phenylephrine is an alpha-1 agonist that is sometimes administered topically prior to surgery to promote mydriasis, but phenylephrine is not approved in the United States in a preservative- and bisulfite-free form for intraocular administration.

It is also desirable to reduce postoperative pain and irritation for patient comfort. Because of this, patients may be treated preoperatively and/or postoperatively with a non-steroidal anti-inflammatory drug (NSAID). Ketorolac is an NSAID that is commercially available in preserved form for ocular use. Acular® from Allergan is a ketorolac tromethamine solution that includes benzalkonium chloride 0.01% as a preservative, available in 3-mL and 6-mL dropper bottles. Bedford Laboratories also supplies ketorolac tromethamine in a concentrated form (15 mg or 30 mg in 1 mL or 60 mg or 300 mg in 10 mL) for injection for intravascular or intramuscular administration. Allergan supplies a preservative-free 0.45% ketorolac tromethamine ophthalmic solution, which is formulated with carboxymethylcellulose sodium, sodium chloride, sodium citrate dehydrate, in individual-use vials under the tradename Acuvail®. Some ophthalmic surgeons also use topical NSAIDs preoperatively in an attempt to preempt intraoperative miosis. This approach to miosis prevention is not optimal because intraoperative irrigation solution washes out preoperatively delivered agents from the areas within the eye that are bathed by the irrigation solution.

Approved by FDA in 2014, OMIDRIA™ (phenylephrine and ketorolac injection) 1%/0.3%), Omeros Corporation, is an alpha 1-adrenergic receptor agonist and nonselective cyclooxygenase inhibitor indicated for maintaining pupil size by preventing intraoperative miosis and for reducing postoperative pain. OMIDRIA™ is added to standard irrigation solution used during cataract surgery or intraocular lens replacement. OMIDRIA™ is not currently indicated for the reduction of postoperative inflammation.

III. SUMMARY OF THE INVENTION

The present invention provides a method for inhibiting a postoperative inflammatory condition following an ophthalmologic surgical procedure. The method includes identifying a subject with an elevated risk of suffering from a postoperative inflammatory condition, which identification may be made preoperatively based on a preexisting physiologic condition or characteristic, prior treatment history, or pharmacologic history, and administering intraocularly to the subject during an ophthalmologic surgical procedure a solution including a nonsteroidal anti-inflammatory drug (NSAID) and an alpha-1 adrenergic receptor agonist mydriatic agent in an intraocular irrigation carrier. The NSAID and the mydriatic agent are included in the solution in amounts sufficient to maintain intraoperative pupil diameter by promoting mydriasis and inhibiting miosis, such as maintaining an intraoperative pupil diameter of at least 6.0 mm during the procedure, and a sufficient amount of the solution is administered for uptake of an amount of the NSAID in ocular tissues sufficient for inhibition of cyclooxygenases for a period of at least six hours postoperatively, thereby inhibiting the postoperative inflammatory condition. In other embodiments of the invention, the identification of an elevated risk of postoperative inflammation may occur during the procedure based on the nature of trauma incurred during the procedure. In still other embodiments, the identification of an elevated risk of a postoperative inflammatory condition may be made intraoperatively and/or preoperatively.

Suitable NSAIDs for use in the solution administered in accordance with the present invention include flurbiprofen, suprofen, diclofenac, ketoprofen, ketorolac, indomethacin, nepafenac and bromfenac, and suitable alpha-1 adrenergic receptor agonists include phenylephrine, epinephrine, oxymetazoline and naphazoline. In a preferred embodiment of the invention, the NSAID is ketorolac and the mydriatic agent is phenylephrine. In another embodiment the solution includes phenylephrine at a concentration of from 240 to 720 µM and ketorolac at a concentration of from 44 to 134 µM. The phenylephrine and ketorolac may be suitably included at a molar ratio of from 3:1 to 10:1 phenylephrine to ketorolac.

In one embodiment of the present invention, administration of the solution results in at least 85%, and preferably at least 90%, inhibition of baseline cyclooxygenase-1 (COX-1) and cyclooxygenase-2 (COX-2) activity in ocular tissues for a period of at least six hours postoperatively. In another embodiment of the present invention, administration of the solution results in at least 85%, and preferably at least 90%, inhibition of baseline COX-1 and COX-2 activity in ocular tissues for a period of at least seven hours postoperatively. In another embodiment of the present invention, administration of the solution results in at least 85% inhibition of baseline COX-1 and COX-2 activity in ocular tissues for a period of at least eight hours postoperatively. In another embodiment of the present invention, administration of the solution results in at least 90% inhibition of baseline COX-1 and COX-2 activity in ocular tissues for a period of at least eight hours postoperatively. In still another embodiment, administration of the solution results in at least 85% inhibition of baseline COX-1 and COX-2 activity in ocular tissues for a period of at least ten hours postoperatively.

The method of the present invention may be used in any ophthalmologic surgical procedure associated with a risk of postoperative inflammation, including procedures requiring pupil dilation and associated with postoperative inflammation, such as cataract extraction and lens replacement, refractive lens exchange, vitrectomy, retinal photocoagulation, retinal detachment repair, macular hole repair, retroiris tumor or mass removal, posterior sclerotomy and optic neurotomy, or in connection with the inhibition of inflammatory conditions resulting from intravitreal injections. In some embodiments, the solution of the present invention is administered to irrigate intraocular tissues during the procedure, such as continuously throughout the procedure. In other embodiments, solution of the present invention is administered by intraocular injection as part of the procedure. In still other embodiments, the solution of the present invention is administered by irrigation of intraocular tissues during the procedure followed by intraocular injection of a bolus of the solution at the end of the procedure. In still another embodiment, the solution of the present invention is administered by postoperative injection of a bolus of the solution at the end of the procedure, for example following the identification of the patient being at risk of a postoperative inflammatory condition due to trauma incurred intraoperatively. In still another embodiment, the solution is administered by intraocular injection preoperatively, intraoperatively and/or postoperatively.

In another aspect of the invention, the method is used in a procedure selected from vitrectomy, retinal photocoagulation, retinal detachment repair, macular hole repair, retroiris tumor or mass removal, posterior sclerotomy and optic neurotomy, or in connection with the inhibition of inflammatory conditions resulting from intravitreal injections.

Postoperative inflammatory conditions inhibited by the methods of the present invention include, for example, toxic anterior-segment syndrome, cystoid macular edema including nonpseudophakic cystoid macular edema and pseudophakic (Irvine-Gass) cystoid macular edema, acute endophthalmitis, posterior capsule opacification, anterior capsule contraction, herpes simplex virus keratitis after cataract surgery, postsurgical hypotony, nylon suture toxicity, long-term corneal endothelial cell loss after cataract surgery, corneal edema, iris chafing, corneo-retinal inflammatory syndrome, scleritis, episcleritis, vitreous wick syndrome, post-operational acute iridocyclitis, uveitis, epiretinal deposits after cataract extraction, reiterative membranous proliferation with giant-cell deposits, toxic vitreitis, posterior synechia, postoperative intraocular fibrin formation, incisional fibrosis, complications of macular hole surgery, choroidal effusion, and hypopyon.

In other embodiments, the subject is identified as having an elevated risk of a postoperative inflammatory condition because of a preoperative physiologic condition or characteristic including small pupil diameter (e.g., a dilated preoperative pupil diameter of less than 6 mm), floppy iris syndrome, uveitis, retinal vein occlusion, epiretinal membrane, advanced age (e.g., over 65, elderly or geriatric), diabetes mellitus, diabetic macular edema, diabetic retinopathy, macular degeneration, or systemic hypertension; a preoperative treatment history including previous ocular surgery or pharmacologic treatment with an alpha-1-adrenergic receptor antagonist or latanoprost; surgical trauma including posterior capsule rupture, secondary capsulotomy, iris incarceration, retained lens material, or vitreous loss; and the surgical placement of nylon sutures, iris-fixated intraocular lens or an anterior chamber intraocular lens.

In a further aspect of the invention, the subject is identified as having an elevated risk of a postoperative inflammatory condition because of a preoperative physiologic condition or characteristic selected from small pupil diameter (e.g., a dilated preoperative pupil diameter of less than 6 mm), floppy iris syndrome, uveitis, retinal vein occlusion, epiretinal membrane, diabetic macular edema, diabetic retinopathy, macular degeneration, or systemic hypertension; a preoperative treatment history including previous ocular surgery or pharmacologic treatment with an alpha-1-adrenergic receptor antagonist or latanoprost; surgical trauma including posterior capsule rupture, secondary capsulotomy, iris incarceration, retained lens material, or vitreous loss; and the surgical placement of nylon sutures, iris-fixated intraocular lens or an anterior chamber intraocular lens.

The present invention also provides a method for inhibiting a postoperative inflammatory condition following an ophthalmologic surgical procedure by identifying a subject with a physiologic risk of suffering from a postoperative inflammatory condition and administering intraocularly to the subject during an ophthalmologic surgical procedure a solution including a nonsteroidal anti-inflammatory drug (NSAID) and an alpha-1 adrenergic receptor agonist mydriatic agent in an intraocular irrigation carrier, wherein the NSAID and the mydriatic agent are included in the solution in amounts sufficient for the maintenance of intraoperative pupil diameter due to the intraoperative promotion of mydriasis by the mydriatic agent and the intraoperative inhibition of miosis by the NSAID, thereby reducing intraoperative trauma, and for the inhibition of the postoperative inflammatory condition by the intraoperative and postoperative anti-inflammatory effect of the NSAID.

The present invention provides a method for inhibiting a postoperative inflammatory condition following an ophthalmologic surgical procedure by intraocular administration during an ophthalmologic surgical procedure, to a subject at risk of a postoperative inflammatory condition, a solution including a nonsteroidal anti-inflammatory drug (NSAID)

and an alpha-1 adrenergic receptor agonist mydriatic agent in an intraocular irrigation carrier. The NSAID and the mydriatic agent are included in the solution in amounts sufficient to maintain intraoperative pupil diameter by promoting mydriasis and inhibiting miosis, and a sufficient amount of the solution is administered for uptake of an amount of the NSAID in ocular tissues sufficient for inhibition of cyclooxygenases for a period of at least six hours postoperatively, thereby inhibiting the postoperative inflammatory condition.

IV. BRIEF DESCRIPTION OF THE DRAWINGS

Figure 2:
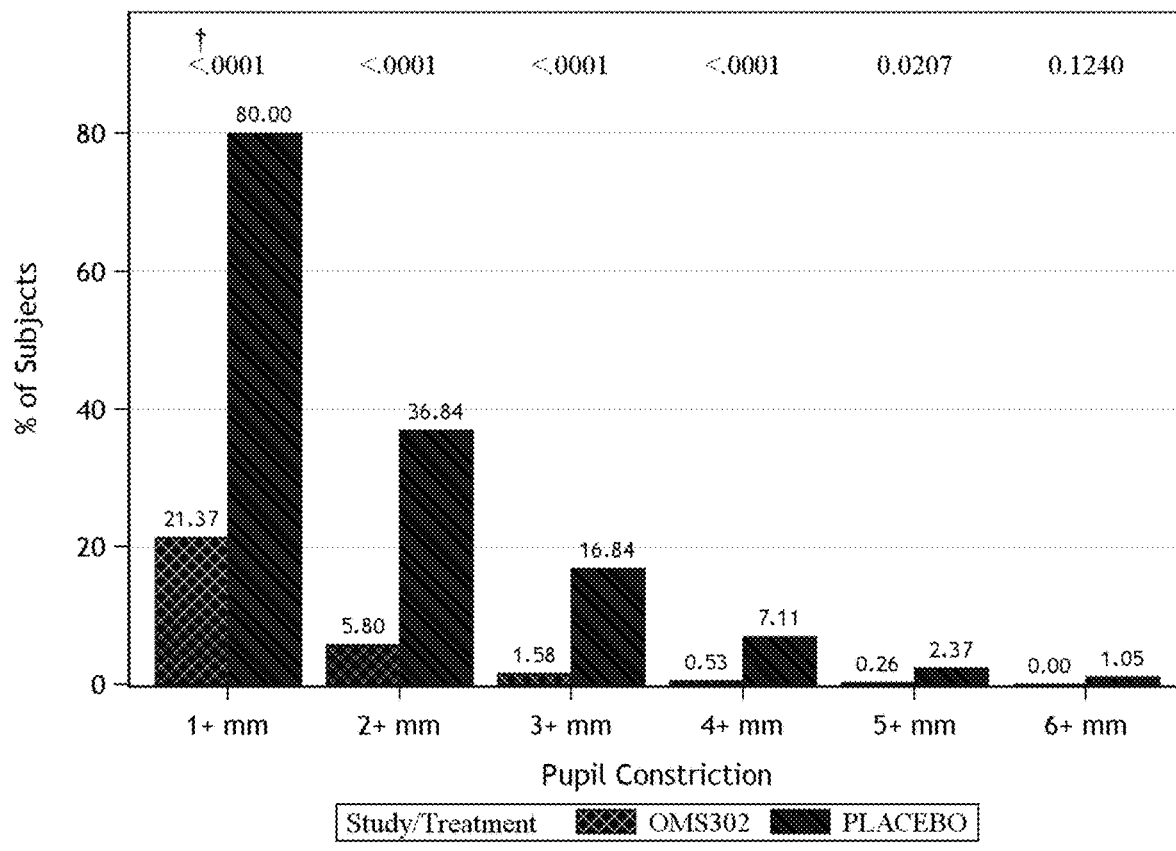
Figure 3:
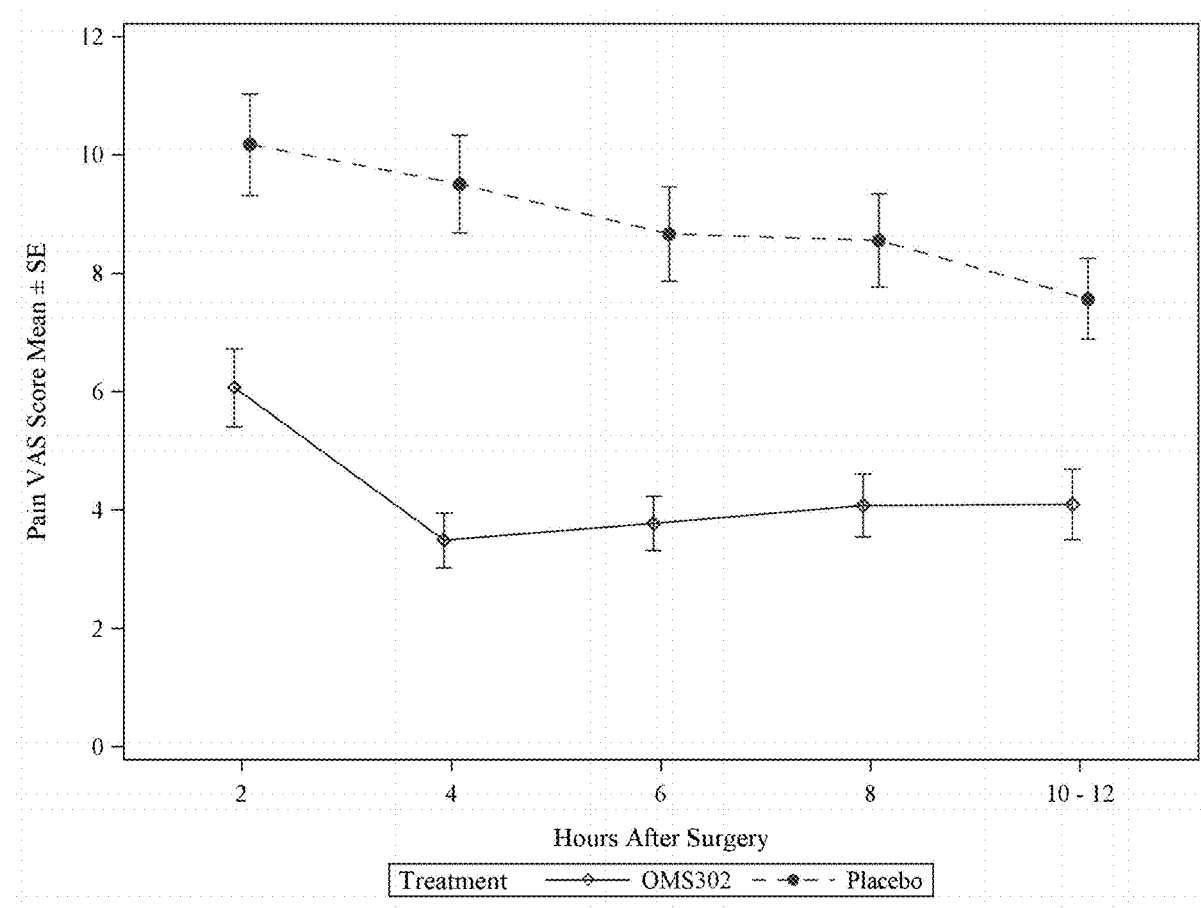

The present invention will now be described in greater detail, by way of example, with reference to the accompanying drawings in which:

FIGS. 1-3 provide results from the clinical studies of Example 1. FIG. 1 illustrates the mean (±SEM) change from baseline in mean pupil diameter (PD) over time to the end of surgery. Pupil diameters were measured at 1-minute intervals from baseline to the end of the procedure and at the end of cortical cleanup from a video recording of the subject's surgery. FIG. 2 illustrates the maximum intraoperative pupil constriction at any time during surgery resulting from the studies. FIG. 3 illustrates the mean ocular pain visual analog scale (VAS) scores during the early postoperative period (full analysis set population).

Figure 4:
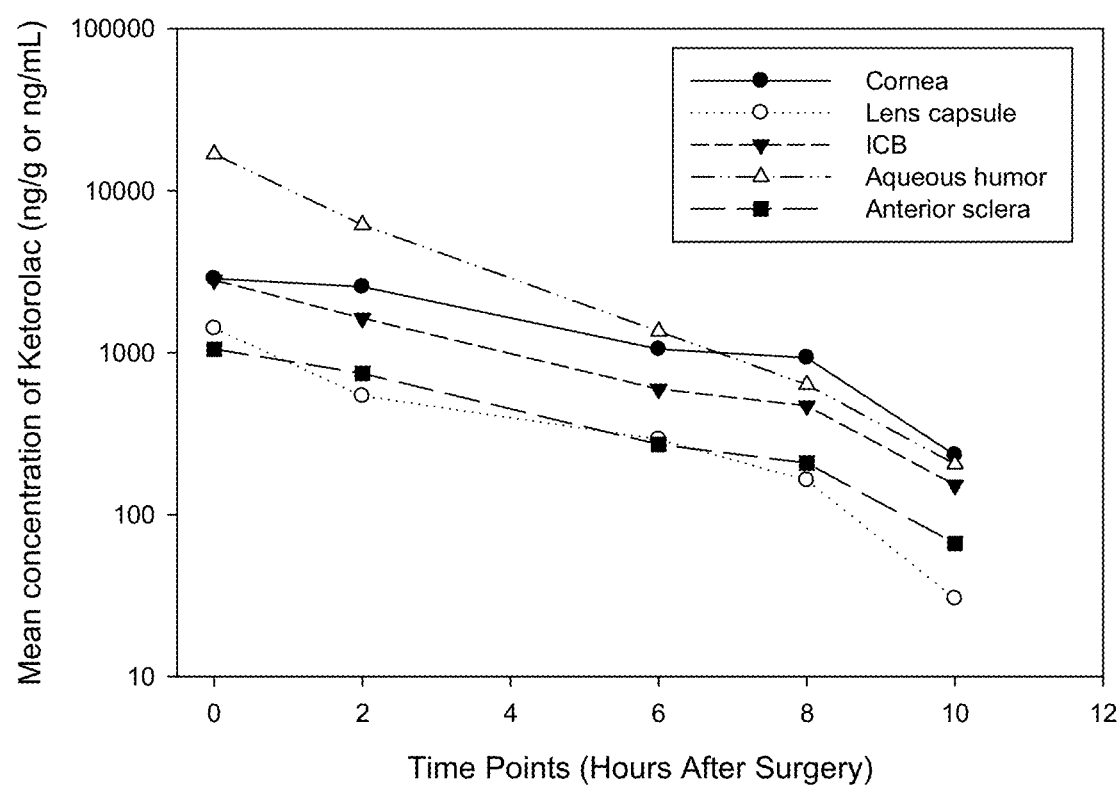
Figure 5:
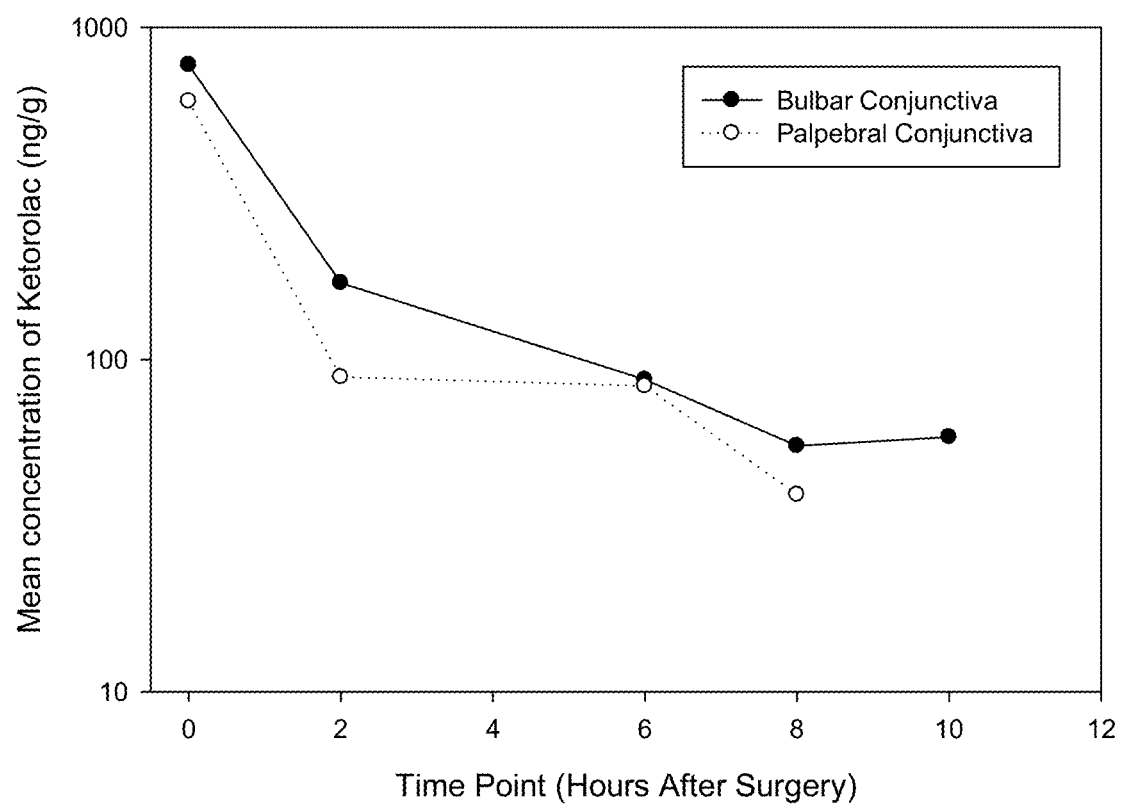
Figure 6:
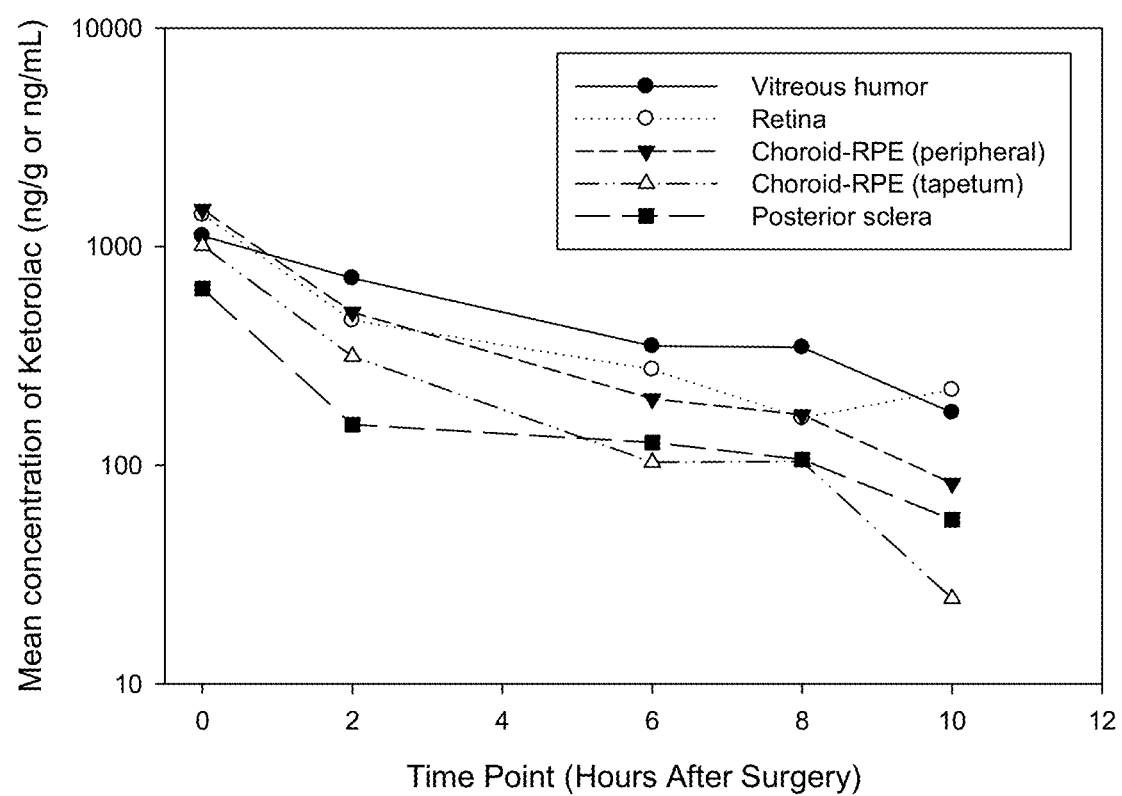
Figure 7:
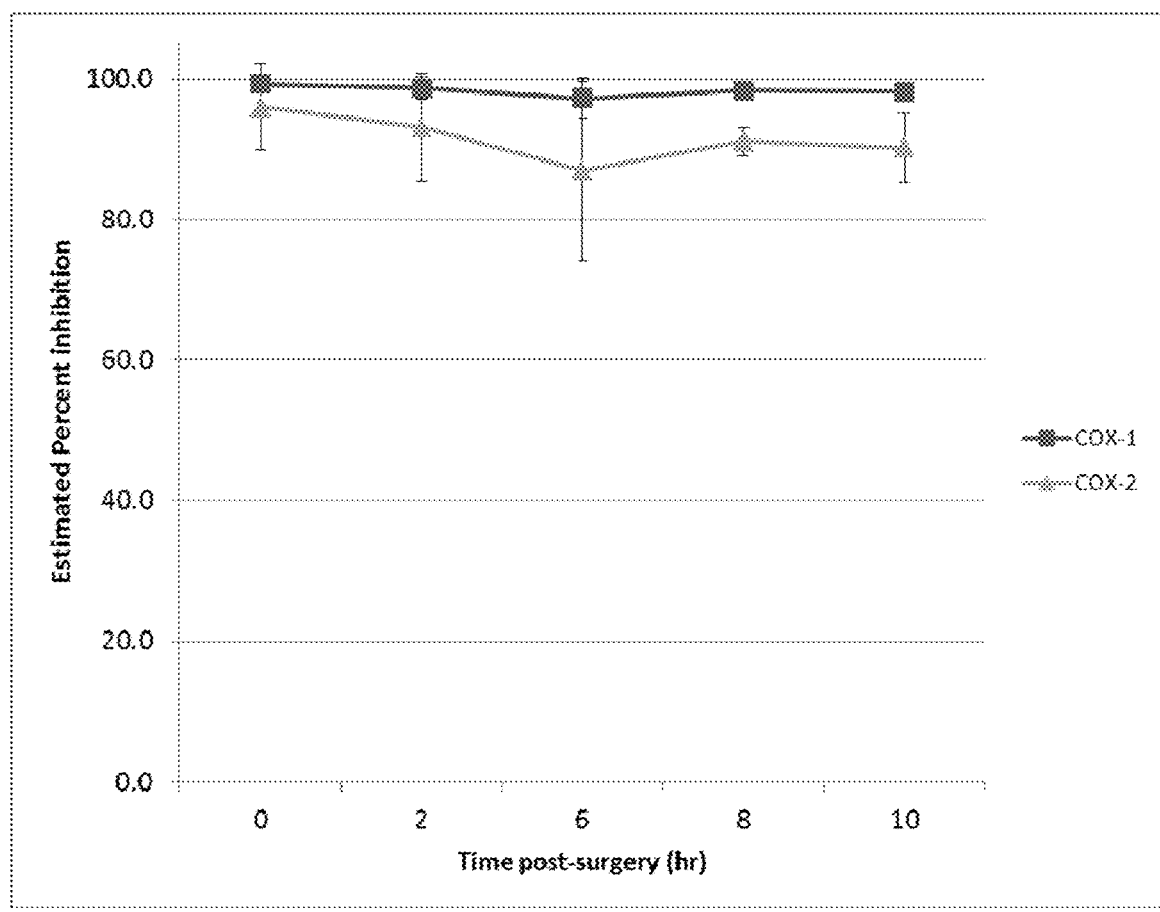

FIGS. 4-7 provide results from the intracameral dog study of Example 2, and illustrate the mean concentrations of ketorolac in ocular tissues of female dogs at specified time points after the intracameral dosing of phenylephrine 1.0%/ketorolac 0.3% injection in balanced salt solution. FIG. 4 shows ketorolac concentrations in the cornea, lens capsule, iris-ciliary body (ICB), aqueous humor, and anterior sclera. FIG. 5 shows ketorolac concentrations in the bulbar and palpebral conjunctiva. FIG. 6 shows ketorolac concentrations in the vitreous humor, retina, choroid-RPE (peripheral), choroid-RPE (tapetum), and posterior sclera. FIG. 7 shows the mean percent inhibition of COX-1 and COX-2 in retinal tissues at t=0 through t=10 hours.

V. DETAILED DESCRIPTION

The present invention provides a method for inhibiting a postoperative inflammatory condition following an ophthalmologic surgical procedure by intraocular administration during an ophthalmologic surgical procedure, to a subject at risk of a postoperative inflammatory condition, a solution including a nonsteroidal anti-inflammatory drug (NSAID) and an alpha-1 adrenergic receptor agonist mydriatic agent in an intraocular irrigation carrier. The NSAID and the mydriatic agent are included in the solution in amounts sufficient to maintain intraoperative pupil diameter by promoting mydriasis and inhibiting miosis, thereby reducing the potential for inflammation-inducing trauma to intraocular structures. A sufficient amount of the solution is administered for uptake of an amount of the NSAID in ocular tissues sufficient for inhibition of cyclooxygenases for a period of at least six hours postoperatively, thereby inhibiting or reducing the likelihood or severity of the postoperative inflammatory condition.

Ophthalmologic Surgical Procedures

The present invention may be utilized in a variety of ophthalmologic surgical procedures that are associated with the occurrence of postoperative inflammatory conditions, including anterior segment procedures performed in the anterior chamber or posterior chamber of the eye, and procedures performed in the posterior segment of the eye, such as retinal procedures. In many cases the procedure is an intracameral procedure. Suitably the ophthalmologic surgical procedure during which the method of the present invention is used is a procedure requiring dilation or mydriasis of the pupil, to provide the surgeon an expanded operative field and visualization of intraocular structures through the dilated pupil. In accordance with the present invention, the solution is administered intraocularly by irrigation and/or injection during the procedure to maintain pupil diameter by promoting mydriasis and inhibiting miosis, thereby reducing surgical trauma to the iris and intraocular structures manipulated through the iris. The solution of the present invention may be administered into the anterior segment of the eye, in particular into the anterior chamber or posterior chamber of the eye, or into the posterior segment of the eye.

Examples of procedures requiring pupil dilation and associated with postoperative inflammation suitable for practice of the present invention include cataract extraction and lens replacement (CELR), refractive lens exchange (RLE), vitrectomy, retinal photocoagulation, retinal detachment repair, macular hole repair, retroiris tumor or mass removal, posterior sclerotomy and optic neurotomy. CELR and RLE may involve femtosecond or scalpel incision, phacoemulsification for lens removal and intraocular lens (IOL) replacement. The present invention may also be used in connection with the inhibition of inflammatory conditions resulting from intravitreal injection, by injecting the solution of the present invention together or concurrently with, or immediately preceding or following, the injection of one or more other therapeutic agents, such as an anti-vascular endothelial growth factor (anti-VEGF) such as ranibizumab.

Ophthalmic surgeons typically use preoperative treatment with mydriatic medications to dilate the pupil before surgery. Behndig, A., et al., "Intracameral mydriatics in cataract surgery," *Cataract Surgery*. Zaidi F. (ed.), Rijeka, Croatia: InTech 2013:149-172. The larger and longer the pupil stays dilated with one or more mydriatic agents, the easier and less risky the procedure. Pupil constriction during surgery makes the procedure more difficult and increases the risk of additional complications. (Behndig 2013)

Postoperative Inflammation

Most cataract procedures are routine and uncomplicated. Patalano, V. J., "The risks and benefits of cataract surgery," *Digital Journal of Ophthalmology*, http://www.djo.harvard-.edu/site.php?url=/patients/pi/408, Accessed Jun. 26, 2014; A.D.A.M., Inc., "Cataracts In-depth report," *The New York Times*, http://www.nytimes.com/health/guides/disease/cataract/print.html, accessed Jun. 26, 2014. But the occurrence of intraoperative complications is often unpredictable and estimated to be associated with 3.8% of cataract procedures in the United States. (Patalano 2014); Greenberg, P. B., et al., "Prevalence and predictors of ocular complications associated with cataract surgery in United States veterans," *Ophthalmology* 118(3):507-514 (2011).

Intraoperative miosis makes the cataract surgical procedure more difficult by shrinking the surgeon's visual field and working space. (Behndig 2013) A small pupil during surgery is associated with increased risk of intraoperative complications, including posterior capsule rupture and vitreous loss. Artzen, D., et al., "Capsule complication during cataract surgery: Case-control study of preoperative and intraoperative risk factors: Swedish Capsule Rupture Study Group report 2," *J Cataract Refract Surg* 35(10):1688-1693 (2009); Zare, M., et al., "Risk factors for posterior capsule rupture and vitreous loss during phacoemulsification," *J Ophthalmic Vis Res.* 4(4):208-212 (2009). Reduced visibility and room for surgical maneuvering may also lead to an increased chance of losing a portion of the lens or the whole lens nucleus into the vitreous cavity (dropping the nucleus) or causing injury to the iris. (Behndig 2013)

Intraoperative miosis is frequently associated with intraoperative floppy iris syndrome (IFIS). Eyes with IFIS have loose, billowy iris tissue with increased risk of prolapse and pupil constriction during surgery. Chang, D. F., Campbell, J. R., "Intraoperative floppy iris syndrome associated with tamsulosin," *J Cataract Refract Surg* 31(4):664-673.22 (2005); Chang, D. F., et al., "Prospective multicenter evaluation of cataract surgery in patients taking tamsulosin (Flomax)" *Ophthalmology* 114(5):957-964 (2007). The number of IFIS cases is known to be especially high among patients who have received treatment with an α1-adrenergic receptor antagonist, such as tamsulosin (Flomax). (Chang 2005); Haridas, A, et al., "Intraoperative floppy iris syndrome (IFIS) in patients receiving tamsulosin or doxazosin-a UK-based comparison of incidence and complication rates" *Graefes Arch Clin Exp Ophthalmol* 251(6):1541-1545 (2013). Tamsulosin is used for the treatment of patients with benign prostatic hyperplasia (noncancerous enlargement of the prostate). Significant intraoperative miosis has been shown to occur in more than 70% of these high-risk patients, even when surgery was performed by highly experienced cataract surgeons. (Chang 2007).

Surgical trauma causes intraocular inflammation, even if the procedure is routine and uncomplicated. Lobo, C., "Pseudophakic cystoid macular edema," *Ophthalmologica* 227(2):61-67 (2012); Miyake, K., Ibaraki, N., "Prostaglandins and cystoid macular edema" *Surv Ophthalmol* 2(47 suppl 1):S203-S18 (2002). Inflammation usually begins in the anterior chamber, either at the site of surgical entry or due to direct mechanical stimulation of intraocular structures such as the iris or ciliary body. Early inflammatory pathways are self-perpetuating, which means that inflammation initially grows in intensity and spreads from the anterior chamber to the vitreous and retina. (Lobo 2012); (Miyake 2002).

Inflammation is associated with vessel dilation and vascular leakage. When the eye is inflamed after surgery, retinal vessels leak and the accumulation of excess fluid causes retinal swelling, or edema. (Lobo 2012); (Miyake 2002). Swelling can include the macula, a specialized zone of the central retina that provides sharp detailed vision used in tasks like reading or driving. Retinal swelling that involves the macula is called macular edema. Cystoid macular edema (CME) is defined by the presence of anatomically distinct fluid pockets, or cysts. Ismail, R., Sallam, A., "Complications associated with cataract surgery," *Cataract Surgery*, Zaidi F. (ed.), Rijeka, Croatia: InTech 2013:221-244. Inflammation and increased levels of intraocular prostaglandins after cataract surgery have been identified as a cause of CME, and there is an association between severe anterior ocular inflammation and postsurgical CME. Rossetti, L., Autelitano, A., "Cystoid macular edema following cataract surgery," *Opin Ophthalmol* 11:65-72 (2000).

Cystoid macular edema (CME) is a primary cause of reduced vision following both cataract and successful vitreoretinal surgery. Loewenstein, A., Zur, D., "Postsurgical Cystoid Macular Edema," *Macular Edema, Dev Ophthalmol.*, Coscas, G. (ed.), Basel, Karger 2010:148-159. CME also remains a problem following capsulotomy, penetrating keratoplasty, scleral buckling, filtering procedures, and panretinal photocoagulation. (Loewenstein 2010); Shimura, M., et al., "Panretinal photocoagulation induces pro-inflammatory cytokines and macular thickening in high-risk proliferative diabetic retinopathy," *Graefes Arch Clin Exp Ophthalmol* 11:65-72 (2000). Estimates of postoperative CME incidence depend on the definition and the method of detection. Studies estimate the prevalence of CME after cataract surgery to be between 4% and 20%. Wielders, L., et al., "Prevention of CME after cataract surgery," *Cataract Refract Surg Today Eur.* 53-55 (2013). CME does not lead to decreased vision in every case, or decreased vision may be minor and imperceptible to the patient. Clinically significant macular edema is associated with visual impairment and estimated to occur in up to 5.8% of eyes after cataract surgery. (Lobo 2012); (Wielders 2013).

An in vivo study evaluated prostaglandin accumulation in the aqueous humor following paracentesis in rabbits as a model of ocular surgical trauma. The concentration of $PGE_2$ in the aqueous humor peaked at one hour following paracentesis and remained substantially elevated for seven hours post paracentesis, approaching baseline levels 48 hours after surgical insult. Graff, G. et al., "Transient loss of prostaglandin synthetic capacity in rabbit iris-ciliary body following anterior chamber paracentesis," *Ocular Immunology and Inflammation* 6(4):227-238 (1998). This study illustrates that once the inflammatory cascade is initiated during ocular surgical trauma, prostaglandin levels remain elevated for a prolonged period, potentially leading to undesired postoperative conditions associated with excess inflammation.

Postoperative Inflammatory Conditions

Excess inflammation induced by ophthalmologic surgery can result in a number of undesired postoperative conditions, and the methods and composition of the present invention may be used to inhibit or reduce the severity or incidence of these conditions.

Toxic anterior segment syndrome (TASS) is an acute postoperative inflammatory reaction in which a noninfectious substance enters the anterior segment and induces toxic damage to the intraocular tissues. Almost all cases occur after uneventful cataract surgery, and, more recently, it has been reported after phakic intraocular lens implantation. This syndrome was previously defined by other names, such as sterile endophthalmitis or postoperative uveitis of unknown cause. Furthermore, a condition termed toxic endothelial cell destruction (TECD) syndrome has been described and is believed to be a variant of TASS. Non-steroidal anti-inflammatory drops have been shown to be a helpful adjunct in several cases of TASS, supporting that TASS is mediated by inflammation. Al-Ghouri, A. R., M.D., "Toxic Anterior Segment Syndrome," http://emedicine.medscape.com/article/1190343-overview, accessed Nov. 23, 2014.

Cystoid macular edema (CME) is a painless condition in which swelling or thickening occurs of the central retina (macula) and is usually associated with blurred or distorted central vision. Less common symptoms include metamorphopsia, micropsia, scotomata, and photophobia. CME is a relatively common condition and is frequently associated with various ocular conditions, such as age-related macular degeneration (AMD), uveitis, epiretinal membrane, vitreomacular traction, diabetes, retinal vein occlusion, medicine-related, or following ocular surgery. When CME develops following cataract surgery and its cause is thought to be directly related to the surgery, it is referred to as Irvine-Gass syndrome or pseudophakic CME. Medical therapy of Irvine-Gass syndrome includes NSAIDs, corticosteroids, and carbonic anhydrase inhibitors. Recent advances in cataract surgery, such as phacoemulsification, small-incision surgery and advances in foldable intraocular lenses, have resulted in the decrease of physical trauma associated with cataract surgery. The decrease in the physical surgical trauma decreases the release of prostaglandins, which are the main players in postoperative ocular inflammation. However, postoperative inflammation continues to be a cause of patient discomfort, delayed recovery and, in some cases, suboptimal visual results. Left untreated, this inflammation might interfere with patients' rehabilitation and/or contribute to the development of other complications, such as cystoid macular edema. Topically applied NSAIDs are commonly used in the management and prevention of noninfectious ocular inflammation and cystoid macular edema following cataract surgery. Colin, J., "The Role of NSAIDs in the Management of Postoperative Ophthalmic Inflammation," *Drugs* 67(9):1291-308 (2007).

Although the most common cause of cystoid macular edema (CME) is due to Irvine-Gass syndrome of CME after cataract extraction or other intraocular surgery, i.e., pseudophakic cystoid macular edema, numerous other conditions are associated with the clinical appearance of fluid-filled cystoid spaces in the macular region, i.e., nonpseudophakic cystoid macular edema. CME is a final common pathway of many intraocular diseases, usually involving the retinal vasculature. The appearance can differ somewhat, depending on the etiology, however, CME can appear as a nonspecific clinical finding. If the cause of CME is not obvious, detailed ophthalmoscopy and, occasionally, ancillary testing may be necessary to identify the cause. The most common drugs used to treat CME include steroids, nonsteroidal anti-inflammatory drugs (NSAIDs), and acetazolamide. Roth, D. B., M.D., "Nonpseudophakic Cystoid Macular Edema," http://emedicine.medscape.com/article/1225735-overview#showall, accessed Nov. 23, 2014.

Inflammation also appears to play a role in acute postoperative endophthalmitis, and the inventors believe that the present invention may be suitable for ameliorating this condition. The use of intravitreal dexamethasone in the treatment of acute postoperative endophthalmitis remains controversial. Clinicians have used this short-acting corticosteroid to inhibit the inflammatory effects of bacterial endotoxins, host factors, and antibiotics. In a rabbit model of virulent infectious endophthalmitis, dexamethasone was shown to decrease elimination of intraocular vancomycin through the trabecular meshwork, suggesting a new potential benefit to steroid administration. Clark, W. L., M.D., "Postoperative Endophthalmitis Treatment & Management," http://emedicine.medscape.com/article/1201260-treatment, accessed Nov. 23, 2014. Nonsteroidal anti-inflammatory drugs may offer equivalent anti-inflammatory efficacy (for both postoperative inflammation and cystoid macular edema) without the typically corticosteroid-associated adverse events. Rowen, S., "Preoperative and Postoperative Medications Used for Cataract Surgery," *Curr Opin Ophthalmol.* 10(1):29-35 (1999).

The present invention may also suitably be used to inhibit postoperative posterior capsule opacification or anterior capsule contraction. In about 20 percent of patients, the posterior portion of the capsule becomes hazy some time during cataract surgery recovery or even months later, causing posterior capsule opacification. Posterior capsule opacification occurs because lens epithelial cells, remaining after cataract surgery, have grown on the capsule. Knobbe, C. A., M.D., "Cataract Surgery Complications," http://www.allaboutvision.com/conditions/cataract-complications.htm, accessed Nov. 23, 2014. Sustained-release celecoxib (an NSAID) from incubated acrylic intraocular lenses has been shown to suppress lens epithelial cell growth in an ex vivo model of posterior capsule opacity. Davis, J. L., et al., "Sustained-release Celecoxib From Incubated Acrylic Intraocular Lenses Suppresses Lens Epithelial Cell Growth in an Ex Vivo Model of Posterior Capsule Opacity," *J Ocul Pharmacol Ther.* 28(4):359-68 (2012).

The present invention may also be suitably used to inhibit herpes simplex virus keratitis after cataract surgery. Ocular infection with herpes simplex virus (HSV) results in a blinding immunoinflammatory stromal keratitis (SK) lesion. Early preclinical events include polymorphonuclear neutrophil (PMN) infiltration and neovascularization in the corneal stroma. HSV infection of the cornea has been demonstrated to result in the upregulation of the cyclooxygenase 2 (COX-2) enzyme. The induction of COX-2 by HSV infection is a critical event, since inhibition of COX-2 with a selective inhibitor has been shown to reduce corneal angiogenesis and SK severity. The administration of a COX-2 inhibitor has been shown to result in reduced PMN infiltration into the cornea as well as diminished corneal vascular endothelial growth factor levels, likely accounting for the reduced angiogenic response. Biswas, P. S., et al, "Role of Inflammatory Cytokine-induced Cyclooxygenase 2 in the Ocular Immunopathologic Disease Herpetic Stromal Keratitis," *J Virol* 79(16):10589-600 (2005).

The nonsteroidal anti-inflammatory drug ketorolac may prevent post-surgical hypotony due to cyclooxygenase products that are released during cataract surgery and other procedures, indicating further utility for the present invention. A study evaluating inhibition of $PGE_2$ production by ketorolac, bromfenac and nepafenac in patients undergoing phacoemulsification demonstrated that ketorolac 0.45% achieved the greatest inhibition of $PGE_2$ compared to nepafenac 0.1% and bromfenac 0.09. Bucci, F. A., Jr., et al., "Prostaglandin E2 Inhibition of Ketorolac 0.45%, Bromfenac 0.09%, and Nepafenac 0.1% in Patients Undergoing Phacoemulsification," *Adv Ther* 28(12):1089-95 (2011). The possibility of an acute increase in intraocular pressure (IOP) following laser iridotomy is well known. A study has shown that laser irradiation of the iris itself can also cause ocular hypotony, so that this phenomenon may be another explanation of the IOP response after peripheral iridoplasty. Kim, Y. Y., et al., "Biphasic Intraocular Pressure Response to Laser Irradiation of the Iris in Rabbits," *Ophthalmic Res* 27(4):243-8 (1995).

Nylon suture toxicity may also result in postoperative inflammation and be suitably inhibited by use of the present invention. A cluster of symptoms and signs that developed in 10 of 105 consecutive patients (9.5%) who underwent uncomplicated planned extracapsular cataract extraction (ECCE) with posterior chamber intraocular lens (PC IOL) implants has been reported as appearing to be related to wound closure. These signs and symptoms included foreign body sensation, conjunctival injection and infiltrates localized to the scleral wound, and scleral excavation underlying the running 10-0 nylon suture possibly resulting from localized scleral edema. The time of clinical presentation ranged from 1 to 6 weeks. Conjunctival stains demonstrated eosinophils and polymorphonuclear leukocytes in some cases. Gram stains, conjunctival cultures, and results of suture toxicology studies were negative. Balyeat, H. D., et al., "Nylon Suture Toxicity After Cataract Surgery," *Ophthalmology* 95(11):1509-14 (1988).

Cataract surgery can in some cases result in long-term corneal endothelial cell loss, while vitrectomy may result in corneal edema, both conditions that may be inhibited by the present invention. Three-day and 1-day dosing of ketorolac has been shown to reduce surgical time, phacoemulsification time and energy, and endothelial cell loss and improved visual acuity in the immediate postoperative period compared with 1-hour predosing or use of a placebo. Donnenfeld, E. D., et al., "Preoperative Ketorolac Tromethamine 0.4% in Phacoemulsification Outcomes: Pharmacokinetic-response Curve," *J Cataract—Refract Surg.* 32(9):1474-82 (2006); Hiraoka, M., et al., "Factors Contributing to Corneal Complications after Vitrectomy in Diabetic Patients," *Jpn J Ophthalmol.* 45(5):492-5 (2001). Ketorolac tromethamine 0.5% ophthalmic solution has been shown to be effective and well-tolerated in controlling postoperative inflammation. Simone, J. N., "Comparison of the Efficacy and Safety of Ketorolac Tromethamine 0.5% and Prednisolone Acetate 1% after Cataract Surgery," *J Cataract Refract Surg.* 25(5): 699-704 (1999).

Intraocular lens implantation may be associated with a corneo-retinal inflammatory syndrome that leads to corneal decompensation and cystoid macular edema. The inflammatory aspects often do not appear striking but manifest as mild ciliary flush, mild flare, moderate cells in the anterior chamber, and moderate vitritis. The cornea will decompensate in the presence of endothelial cell counts which are sufficient to maintain corneal clarity in the non-inflamed eye. Metal-looped lenses and poorly polished lenses cause iris chafing and capillary leakage, which increase the severity of this syndrome. It is postulated that intraocular surgery initiates an inflammatory response that is augmented by certain components of intraocular lenses. The mediation for this increased inflammatory response may be inhibited by both steroidal and non-steroidal anti-inflammatory agents. The presence of white blood cells and their products, such as lysosomal enzymes, may be sufficient to perpetuate the inflammatory response and cause damage to abnormal and normal cells. The presence of protein and its immune components, as well as complement, may be involved in this syndrome. Obstbaum, S. A., et al., "Cystoid Macular Oedema and Ocular Inflammation. The Corneo-Retinal Inflammatory Syndrome," *Trans Ophthalmol Soc U K.* 99(1):187-91(1979).

Postsurgical scleritis and episcleritis may also be inhibited by use of the present invention. A number of cases of necrotic sclerokeratitis following eye surgery have been reported in recently published literature. The condition was presumably triggered by surgical inflammation and caused by localized occlusive vasculitis: in one case deposits of immune complexes in vessel walls were demonstrated. Clinical examination shows disappearance of vessels in affected sclera, together with tissue necrosis. Gregersen, E., et al., "Necrotizing Sclerokeratitis Following Cataract Extraction," *Klin Monbl Augenheilkd.* 193(6):642-4 (1988). In a report of 21 cases, out of a total of 682 cataract patients, of surgically induced diffuse scleritis (SIDS) following planned extracapsular cataract extraction with intraocular lens insertion, the mean age was found to be significantly lower in the patients with SIDS (mean 62.5 years; SD 13.68) when compared with the non-scleritic group (mean 73.6 years, SD 10.2; Mann-Whitney U-test, p=0.0003). There was an association of SIDS with general anesthesia (chi-squared test, p=0.0008). Twenty of the 21 patients with SIDS responded to oral non-steroidal anti-inflammatory agents with good visual result. Scott, J. A., et al., "Surgically Induced Diffuse Scleritis Following Cataract Surgery," *Eye (Lond).* 8 (Pt 3):292-7 (1994).

Vitreous wick syndrome occurs after eye surgery and consists of microscopic wound breakdown, followed by a vitreous prolapse that develops into a vitreous wick, and may also be suitably inhibited by practice of the present invention. Vitreous wick syndrome develops in the setting of trauma, either iatrogenic or noniatrogenic. Vitreous wick syndrome of iatrogenic origin usually follows anterior-segment surgery, though it may also follow subtenon injection and muscle surgery. Corneal wound healing has been documented to be slower on the endothelial side (inner layers). Poor suturing technique is implicated as a major factor for wound breakdown. Tightly compressed corneal wound edges may demonstrate puckering and also may lead to enlargement of suture tracts, promoting tissue necrosis within the suture loop. Once communication between the posterior wound gap and the anterior wound defect occurs (subsequent to tissue necrosis from tight sutures), anterior aqueous fluid may egress; vitreous incarceration may also occur, producing the vitreous wick. Occasionally, complete sloughing of strangulated tissue within the suture loop may occur. Rogue, M. R., M.D., M.B.A., F.P.A.O, "Vitreous Wick Syndrome," http://emedicine.medscape.com/article/1230457-overview#a0101, accessed Nov. 23, 2014. A study comparing the force required to separate corneal wounds after topical applications of nonsteroidal anti-inflammatory drugs or corticosteroids found that steroid treatment caused weaker corneal wound scars than did NSAIDs. McCarey, B. E., et al., "Corneal Wound Healing Strength with Topical Antiinflammatory Drugs," *Cornea* 14(3):290-4 (1995).

Post-operational acute iridocyclitis, or post-surgical inflammation of the iris and ciliary body, also provides a treatment opportunity for the present invention. Evaluation of the adjunctive use of nonsteroidal anti-inflammatory drugs for the treatment of chronic iridocyclitis in 14 patients has been reported, eight of whom had juvenile rheumatoid arthritis and six with idiopathic iridocyclitis. In all patients, the activity of the iridocyclitis improved with the addition of NSAIDs to their treatment regimens, permitting reduction in the dose of corticosteroid drugs. These data suggest that NSAID therapy may have an adjunctive role in the treatment of chronic iridocyclitis in childhood. Olson, N.Y., et al., "Nonsteroidal anti-inflammatory drug therapy in chronic childhood iridocyclitis," *Am J Dis Child* 142(12):1289-92 (1988). Cataract is an early complication of juvenile idiopathic arthritis-associated uveitis. Under strict control of uveitis, IOL implantation is an important alternative in visual rehabilitation for this type of patient. Control of uveitis with NSAIDs before, during and after cataract surgery presents a further utility for the present invention. Kotaniemi, K., et al., "Intraocular Lens Implantation in Patients with Juvenile Idiopathic Arthritis-Associated Uveitis," *Ophthalmic Res.* 38(6):318-23 (2006).

The present invention may additionally be used to inhibit inflammation due to epiretinal deposits after cataract extraction. In a report of two patients identified with epiretinal deposits after cataract extraction where the posterior capsule barrier was breached, inflammation was found to be limited to the posterior segment, and investigative work-up for infective causes was negative. Behera, U. C., "Epiretinal Deposits Post Cataract Extraction," *Retin Cases Brief Rep.* 7(4):359-61 (2013).

Reiterative membranous proliferation with giant-cell deposits may follow some cases of cataract surgery. One report addresses the outcomes of a 72-year-old Japanese woman and a 67-year-old Japanese man who underwent AcrySof IOL (SA60AT) implantation in their eyes (both eyes in the first case and the left eye in the second case) for the treatment of cataract and vitreous opacity with uveitis. Although intraocular inflammation seemed to be successfully controlled, the number of giant-cell deposits on the posterior surface of the posterior capsule was gradually increased with the development of posterior capsular opacification in 5 and 9 months, respectively, and neodymium-doped yttrium-aluminum-garnet (Nd:YAG) laser capsulotomy was required. Iwase, T., "Reiterative Membranous Proliferation With Giant-Cell Deposits on Hydrophobic Acrylic Intraocular Lenses After Triple Procedures in Eyes with Cataracts and Uveitis," *Cutanl Ocul Toxicol.* 29(4): 306-11 (2010).

A report of 11 cases of intraocular inflammation after intravitreal injection indicates another suitable use of the present invention. Only one of these cases involved infectious endophthalmitis with retinal abscess, with all others involving toxic vitreitis. Seven eyes exhibited hypopyon and five disseminated retinal hemorrhages. The toxic reaction occurred within 48 hours after injection, whereas in the endophthalmitis case, it occurred after 72 hours. The cause of this reaction was believed by the reporting authors to be the particular syringe brand used. After changing to another syringe brand, no further cases of toxic vitreitis occurred during the next 6 months. Ness, T., et al., "Toxic Vitreitis Outbreak After Intravitreal Injection," *Retina.* 30(2):332-8 (2010).

A synechia is an eye condition where the iris adheres to either the cornea (i.e., anterior synechia) or lens (i.e., posterior synechia), and instances of this condition following surgical procedures may be inhibited by the present invention. Synechiae can be caused by ocular trauma, iritis or iridocyclitis and may lead to certain types of glaucoma. Topical corticosteroids have conventionally been used to subdue the inflammation. Wikipedia contributors, "Synechia (eye)," *Wikipedia, The Free Encyclopedia*, http://en.wikipedia.org/wiki/Synechia_(eye), accessed Nov. 23, 2014.

The present invention may also be used to inhibit postoperative intraocular fibrin formation. The anti-inflammatory effect of 0.1% diclofenac sodium on anterior inflammation after cataract surgery has been reported. Fibrin precipitation after surgery in patients without systemic or ocular disease was markedly less when diclofenac sodium ophthalmic solution was used in combination with topical corticosteroids. There was also a reduction in fibrin precipitation in other patients, especially in those with diabetes mellitus, primary angle-closure glaucoma, and exfoliation syndrome. Matsuo, K., et al., "Clinical Efficacy of Diclofenac Sodium on Postsurgical Inflammation After Intraocular Lens Implantation," *Refract Surg.* 21(3):309-12 (1995).

Four cases of incisional complications following pars plana vitrectomy illustrate a utility of the present invention for the inhibition of incisional fibrosis. As reported, in each instance excessive fibrosis occurred at the wound site. In one patient, the disorder was mild and did not lead to clinical difficulties during his lifetime; however, in the three severe cases the eyes were lost secondary to intraocular organization (fibrotic changes) and phthisis bulbi. Possible contributing factors include diabetes mellitus, excessive trauma and necrosis at the wound site, postoperative inflammation, and vitreous involvement in the wound. Kreiger, A. E., "Incisional Complications in Pars Plana Vitrectomy," *Mod Probl Ophthalmol.* 18:210-23 (1977).

The present invention may be useful for treating choroidal neovascularization and other complications following surgical treatment for macular holes. In a reported study of complications of vitrectomy surgery for full-thickness macular holes, posterior segment complications were noted in 39 eyes (41%). The incidence of retinal pigment epithelium alteration and retinal detachment were 33% and 11%, respectively. One case of retinal detachment due to a giant retinal tear resulted in a visual acuity of light perception. Other complications included a reopening of the macular hole in two eyes (2%), cystoid macular edema in one eye (1%), a choroidal neovascular membrane in one eye (1%) and endophthalmitis in one eye (1%). Banker, A. S., "Vision-Threatening Complications of Surgery for Full-Thickness Macular Holes. Vitrectomy for Macular Hole Study Group," *Ophthalmology.* 104(9):1442-52 (1997). A pilot study has been reported that suggests that topical ketorolac may supplement the activity of intravitreal ranibizumab in reducing a mean six-month change in central macular thickness in choroidal neovascularization. Russo, A., et al., "A Randomised Controlled Trial of Ranibizumab With and Without Ketorolac Eyedrops for Exudative Age-Related Macular Degeneration," *Br J Ophthalmol.* 97(10):1273-6 (2013).

Choroidal effusion, which is an abnormal accumulation of fluid in the suprachoroidal space, is a common complication of glaucoma surgery and may suitably be inhibited by the practice of the present invention. Choroidal effusion may also arise from other intraocular surgical procedures as well as a number of conditions, including inflammatory and infectious diseases, trauma, neoplasms, drug reactions, and venous congestion. Idiopathic causes fall under the umbrella of uveal effusion syndrome, a rare condition usually considered a diagnosis of exclusion. Reddy, A. C., M.D, "Diagnosis and Management of Choroidal Effusions," http://www.aao.org/publications/eyenet/201211/pearls.cfm?RenderForPrint=1&, accessed Nov. 23, 2014.

Hypopyon is seen as yellowish exudate in the lower part of the anterior chamber of the eye and is formed of inflammatory cells. It is a leukocytic exudate and is a sign of inflammation of the anterior uvea and iris, i.e., iritis, which is a form of anterior uveitis. Hypopyon has been reported in a patient with rheumatoid arthritis undergoing phacoemulsification. This 70-year-old woman was on a maintenance dose of systemic methylprednisolone at the time of uneventful phacoemulsification in the left eye. She developed a sterile hypopyon on the first postoperative day, which was treated aggressively with topical and systemic therapy, resulting in a gradual resolution of the inflammatory response. The patient subsequently had phacoemulsification in the right eye. The only significant difference in the preoperative management this time was that the patient received topical ofloxacin and ketorolac four days before surgery. The postoperative inflammatory response was much more controlled. The patient was continued on ketorolac and prednisolone acetate, resulting in the usual postoperative inflammatory response. Caronia, R. M., "Antiinflammatory Effect of Preoperative Ketorolac in Phacoemulsification," *J Cataract Refract Surg.* 28(10): 1880-1 (2002). This report suggests that the present invention may have utility for inhibition of hypopyon following ocular surgery.

Predisposing Conditions

The present invention also provides a method for inhibiting a postoperative inflammatory condition following an ophthalmologic surgical procedure by identifying a subject with a physiologic risk of suffering from a postoperative inflammatory condition and administering intraocularly to the subject during an ophthalmologic surgical procedure a solution including a nonsteroidal anti-inflammatory drug (NSAID) and an alpha-1 adrenergic receptor agonist mydriatic agent in an intraocular irrigation carrier, wherein the NSAID and the mydriatic agent are included in the solution in amounts sufficient for the inhibition of the postoperative inflammatory condition.

Small pupil size during surgery is also associated with increased risk of intraoperative complication. (Artzen 2009); (Zare 2009). Studies have identified risk factors to help surgeons predict which patients may be at risk of a complication during surgery. Advanced age, previous ocular surgery, and diabetes with ophthalmic manifestations are among patient-related factors that have been associated with increased risk of intraoperative complication. (Greenberg 2011). Individuals with diabetes mellitus (DM) are often predisposed to developing cataracts; over 25% of cataract patients are estimated to also have concomitant DM. *National Diabetes Clearing House*, diabetes.niddk.nih.gov, Accessed on Sep. 30, 2012; Ostri C., et al., "Phacoemulsification cataract surgery in a large cohort of diabetes patients: visual acuity outcomes and prognostic factors," *J Cataract Refract Surg* 37(11):2006-2012 (2011). Individuals with DM who undergo cataract surgery have a greater propensity towards intraoperative miosis than individuals without DM. This may lead to more postoperative complications such as development of postoperative cystoid macular edema, worsening diabetic macular edema, progression to proliferative diabetic retinopathy, and the development of rubeosis iridis. Oetting, T., "Complicated cataract cases. Cataract surgery and diabetes," *ASCRS EyeWorld*, http://www.eyeworld.org/article-cataract-surgery-and-diabetes, Accessed Nov. 25, 2014.

Systemic diseases, intraoperative complications and preexisting ocular conditions are risk factors that influence the development of CME. (Loewenstein 2010). Systemic risk factors for postsurgical CME include diabetes mellitus, which promotes the development of CME even in the absence of diabetic retinopathy. Schmier J., et al., "Evaluation of costs for cystoid macular edema refractory to topical medications," *Ophthalmology* 104:2003-2008 (1997). Systemic hypertension apparently increases the incidence of postsurgical CME. Flach, A., "The incidence, pathogenesis and treatment of cystoid macular edema following cataract surgery," *Trans Am Ophthalmol Soc* 96:557-634 (1998). Systemic hypertension is also a risk factor for retinal vein occlusion, which itself increases CME. (Loewenstein 2010).

Certain surgical complications also raise the risk of CME. Rupture of the posterior capsule, as well as secondary capsulotomy, including YAG capsulotomy, are associated with a higher rate of CME. Vitreous loss increases the prevalence of CME by 10-20%/o. Iris incarceration is an additional risk factor for CME, as are certain types of intraocular lenses, specifically iris-fixated IOLs and anterior chamber IOLs. (Loewenstein 2010). A review of patients with CME following pars plana vitrectomy for retained lens fragments demonstrated that 8% of eyes with a sulcus-fixated posterior chamber IOL implanted at cataract extraction and 46% of eyes with aphakia or an anterior chamber IOL developed CME. Cohen, S., et al., "Cystoid macular edema after pars plana vitrectomy for retained lens fragments," *J Cataract Surg* 32:1521-1526 (2006).

Certain preexisting conditions also increase the risk of postsurgical CME. These conditions may compromise the integrity of the blood-retinal barrier and boost inflammatory activity. These include uveitis, in which CME is the most important cause for poor visual outcomes following cataract surgery. (Loewenstein 2010). As noted above, preoperative diabetic retinopathy considerably increases the risk of onset and persistence of CME (Iliff, W., "Aphakic cystoid macular edema and the operating microscope: is there a connection?" *Trans Am Ophthalmol Soc* 83:476-500(1985)), while a history of retinal vein occlusion and epiretinal membrane (ERM) also predict development of CME. Henderson, B., et al., "Clinical pseudophakic cystoid macular edema. Risk factors for development and duration of treatment," *J Cataract Refract Surg* 33:1550-1558 (2007). The topical use of latanoprost in glaucoma patients has been reported in association with pseudophakic CME. Warwar, R., et al., "Cystoid macular edema and anterior uveitis associated with latanoprost use. Experience and incidence in a retrospective review of 94 patients." *Ophthalmology* 105:263-268 (1998).

In accordance with an aspect of the present invention, a subject to be treated with the NSAID and an alpha-1 adrenergic receptor agonist solution of the invention is identified as having an elevated risk of a postoperative inflammatory condition because of a preoperative physiologic condition or characteristic including small pupil diameter (e.g., a dilated preoperative pupil diameter of less than 6 mm), floppy iris syndrome, uveitis, retinal vein occlusion, epiretinal membrane, advanced age (e.g., over 65, elderly or geriatric), diabetes mellitus, diabetic macular edema, diabetic retinopathy, macular degeneration, or systemic hypertension; a preoperative treatment history including previous ocular surgery or pharmacologic treatment with an al-adrenergic receptor antagonist or latanoprost; surgical trauma including posterior capsule rupture, secondary capsulotomy, iris incarceration, retained lens material, or vitreous loss; and the surgical placement of nylon sutures, iris-fixated intraocular lens or an anterior chamber intraocular lens. As used herein, "elevated risk" of a postoperative inflammatory condition refers to a subject whose risk of experiencing a postoperative inflammatory condition following an ophthalmologic procedure is greater than the mean incidence rate of the same postoperative inflammatory condition in healthy subjects who do not have any predisposing risk characteristics that are undergoing the same procedure.

Subjects at elevated risk of postoperative inflammation may be identified by the surgeon in advance of surgery as having an elevated risk of postoperative inflammation based on the patient's preoperative physiologic condition or characteristic or preoperative treatment history, or the planned placement of sutures or intraocular devices that are associated with an enhanced incidence of postoperative inflammation. Once identified, the surgeon may administer the solution of the present invention during the operative procedure to preemptively decrease or reduce the incidence or severity of postoperative inflammation. Alternately the surgeon may prophylactically administer the solution of the present invention during the operative procedure to address an enhanced risk of postoperative inflammation that may be identified during the procedure due to the nature of surgical trauma, e.g., posterior capsule rupture, secondary capsulotomy, iris incarceration, retained lens material, or vitreous loss, or unplanned use of sutures or devices that are associated with an enhanced incidence of postoperative inflammation.

Pharmacologic Agents

A broad variety of ophthalmologic surgical procedures induce intraocular inflammation. As evidenced by the above described paracentesis study, once the inflammatory cascade is initiated, prostaglandin levels remain elevated for up to seven hours. The method of the present invention provides for the intraoperative delivery of a combination of an NSAID and an alpha-1 adrenergic receptor agonist mydriatic agent. In a preferred embodiment of the invention, the NSAID is ketorolac and the alpha-1 adrenergic receptor agonist mydriatic agent is phenylephrine.

The impact of NSAIDs in inhibiting the formation of prostaglandin by cyclooxygenase (COX) enzymes has been shown in several studies to have an important impact on prevention of CME. Wolf, E. J., et al., "Incidence of visually significant pseudophakic macular edema after uneventful phacoemulsification in patients treated with nepafenac," *J Cataract Refract Surg* 33:1546-1549 (2007); Cervantes-Coste, G., et al., "Inhibition of surgically induced miosis and prevention of postoperative macular edema with nepafenac," *Clin Ophthalmol* 3:219-226(2009); Donnenfeld, E. D., et al., "Preoperative ketorolac tromethamine 0.4% in phacoemulsification outcomes: pharmacokinetic-response curve," *J Cataract Refract Surg.* 32:1474-1482 (2006).

Suitable non-steroidal anti-inflammatory drugs (NSAIDs) for use in the present invention include flurbiprofen, suprofen, diclofenac, ketoprofen, ketorolac, indomethacin, nepafenac and bromfenac. A preferred NSAID is ketorolac. As used herein, "ketorolac" means ketorolac in a salt form, such as ketorolac tromethamine [(+/−)-5-Benzoyl-2,3-dihydro-1H-pyrrolizine-1-carboxylic acid:2-amino-2(hydroxymethyl)-1,3-propanediol (1:1)]. Ketorolac in one formulation of the present invention is included as the ketorolac tromethamine salt [(+/−)-5-Benzoyl-2,3-dihydro-1H-pyrrolizine-1-carboxylic acid:2-amino-2(hydroxymethyl)-1,3-propanediol (1:1)]. Ketorolac is a member of the pyrrolo-pyrrole group of nonsteroidal anti-inflammatory drugs. Ketorolac HCL is a racemic mixture of the R−(+) and S−(−) enantiomers that may exist in three crystal forms, all of which are equally soluble in water. Ketorolac is a nonsteroidal anti-inflammatory that inhibits both cyclooxygenase enzymes (COX-1 and COX-2), and when used in accordance with the present invention results in a decrease in tissue concentrations of prostaglandins to reduce pain due to surgical trauma. Ketorolac, by inhibiting prostaglandin synthesis secondary to ocular surgical insult or direct mechanical stimulation of the iris, also prevents surgically induced miosis when used in accordance with the present invention.

Suitable alpha-1 adrenergic receptor agonists for use as mydriatic agents in the present invention include, for example, phenylephrine, epinephrine, oxymetazoline and naphazoline. A preferred alpha-1 adrenergic receptor agonist is phenylephrine. As used herein, "phenylephrine" means phenylephrine in a salt form, such as phenylephrine HCL [(−)-m-Hydroxy-a-[(methyl amino)methyl]benzyl alcohol hydrochloride]. Phenylephrine is an alpha-1 adrenergic receptor agonist and, in the eye, acts as a mydriatic agent by contracting the radial muscle of the iris.

In accordance with the present invention, the NSAID and alpha-1 adrenergic receptor agonist solution is administered intraocularly by irrigation and/or injection during the procedure to maintain pupil diameter by promoting mydriasis and inhibiting miosis, thereby reducing surgical trauma to the iris and intraocular structures manipulated through the iris. Thus the local intraocular presence of both a mydriatic agent (e.g., phenylephrine) and an anti-miotic agent (e.g., ketorolac) during the surgical procedure provide complimentary mechanisms to preemptively limit trauma-induced inflammation during the procedure. The in vivo study using paracentesis in a rabbit model of surgical trauma described above (Graff 1998) demonstrates that, following ocular surgical trauma, prostaglandin levels remain elevated for a period of up to seven hours. The in vivo study in dogs to determine the concentrations of ketorolac in the retina and other ocular tissues following the intracameral administration of a phenylephrine and ketorolac solution, described in Example 2 below, demonstrates that the intraoperative uptake of ketorolac by retina and other ocular tissues is surprisingly at levels sufficient to inhibit COX-1 and COX-2 levels by at least 90% in ocular tissues for at least 8 hours following drug administration, and by at least 85% in ocular tissues for at least 10 hours following drug administration. Thus the present invention inhibits inflammation during the surgical procedure, both by reducing trauma through complimentary mydriatic and anti-miotic effects and by preemptively inhibiting prostaglandin release, and continues to inhibit inflammation during the period when postsurgical cyclooxygenase levels are most elevated.

Formulations

The NSAID and alpha-1 adrenergic receptor agonist are contained in an aqueous solvent as a carrier to provide a drug composition or solution. The aqueous carrier is suitably water for injection (WFI), which is a sterile, solute-free preparation of distilled water. Alternately, other aqueous carriers that are not harmful to intraocular tissues and which would not adversely affect the stability of the formulation may be used, such as deionized water, or, after first evaluating for potential impact on stability, saline or a balanced salt solution such as that described below.

The solution of the NSAID and alpha-1 adrenergic receptor agonist of the present invention is suitably adjusted to a pH from 5.8 to 6.8, and preferably to about 6.3. Sodium hydroxide and hydrochloric acid may be added as required to adjust the formulation to this pH. The desired pH is suitably maintained by use of a buffering system. One such suitable system is a citrate buffer, including citric acid monohydrate and sodium citrate dehydrate, and another suitable system is a sodium phosphate buffer, including dibasic sodium phosphate and monobasic sodium phosphate. Either buffer system may be used at an appropriate concentration in the range of 10 mM to 100 mM, and suitably may be 20 mM. As described below in Example 1, sodium citrate is a preferred buffer for use in a preservative- and antioxidant-free formulation. The citric acid in the citrate buffer, which has the ability to chelate divalent cations and can thus also prevent oxidation, provides an antioxidant effect as well as a buffering effect. As used herein, the term "antioxidant free" precludes the use of other antioxidants but does not preclude the use of a buffering agent, such as citric acid, that is included as part of the buffering system.

The NSAID and alpha-1 adrenergic receptor agonist solution of the present invention, e.g., a phenylephrine and ketorolac combination drug solution, is suitably diluted into an intraocular irrigation solution by injection into a bag, bottle or other container of an intraocular irrigation solution prior to administration by intraocular irrigation or injection. Suitable intraocular irrigation solutions include saline, lactated Ringer's, balanced salt solution or any other irrigation solution that is compatible with the aqueous formulation and not harmful to ocular tissues. One suitable intraocular irrigation carrier includes one or more, and preferably all, of the following adjuvants: sufficient electrolytes to provide a physiological balanced salt solution; a cellular energy source; a buffering agent; and a free-radical scavenger. One suitable solution (referred to in the examples below as a "balanced salt solution" or "BSS" includes: electrolytes of from 50 to 500 millimolar sodium ions, from 0.1 to 50 millimolar potassium ions, from 0.1 to 5 millimolar calcium ions, from 0.1 to 5 millimolar magnesium ions, from 50 to 500 millimolar chloride ions, and from 0.1 to 10 millimolar phosphate; bicarbonate as a buffer at a concentration of from 10 to 50 millimolar; a cellular energy source selected from included at a concentration of from 10 to 100 mM, and preferably at about 20 mM. An exemplary formulation for use in accordance with the present invention is set forth in Table 1 below. Sodium hydroxide and/or hydrochloric acid may be added when preparing the formulation if necessary to adjust the pH to about 6.3.

TABLE 1

Example Formulation

| Component (USP) added to water for injection | Preferred Concentration | | Suitable Concentrations | | Representative Diluted Dosing Concentration ($\mu m$) | |
|---|---|---|---|---|---|---|
| | mg/mL | mM | mg/mL | mM | Preferred | Suitable |
| Phenylephrine HCl | 12.37 | 60.75 | 9.2-15.5 | 45-76 | 483 | 240-720 |
| Ketorolac tromethamine | 4.24 | 11.25 | 3.2-5.3 | 8.5-14 | 89 | 44-134 |
| Citric acid monohydrate | 0.24* | | 0.12-1.20** | | | |
| Sodium citrate dihydrate | 5.48* | | 2.74-27.4** | | | |

*Corresponding to a 20 mM citrate buffer.
**Corresponding to a 10 mM to 100 mM citrate buffer.

dextrose and glucose, at a concentration of from 1 to 25 millimolar; and glutathione as a free-radical scavenger (i.e., antioxidant) at a concentration of from 0.05 to 5 millimolar.

One example of a suitable method of diluting and administering the preferred phenylephrine and ketorolac composition of the present invention utilizes the formulation of the present invention described in Table 1 below. An aliquot of 4.5 mL of this solution, including 4.0 mL as the intended quantity for single use and 0.5 mL of overfill, is contained within a sterile closed single-use vial and is intended for admixture with irrigation solution for administration during intraocular surgery. From the vial, 4 mL is withdrawn by syringe and mixed with 500 mL of BSS by injection into a 500-mL bag or bottle of BSS to provide a final concentration of 483 $\mu M$ phenylephrine and 89 $\mu M$ ketorolac in the irrigation solution for local delivery to the eye.

In another aspect of the invention, a sterile liquid pharmaceutical formulation for irrigation may be provided in which the phenylephrine and ketorolac are already admixed within an intraocular irrigation carrier, such that it has been diluted to the concentration of each active pharmaceutical ingredient desired for local delivery to intraocular tissues during surgery, and contained within a sterile bag, bottle or other irrigation container. For example, such a formulation for irrigation may include phenylephrine at a concentration of from 30 to 720 $\mu M$ and ketorolac at a concentration of from 10 to 270 $\mu M$, or preferably may include the phenylephrine at a concentration of from 90 to 720 $\mu M$ and the ketorolac at a concentration of from 44 to 134 $\mu M$.

As described above, an exemplary stable, liquid pharmaceutical formulation of the present invention includes phenylephrine and ketorolac in a buffered aqueous carrier. Suitable concentrations of phenylephrine in the combination drug compositions of the present invention range from 10 mM to 500 mM, and preferably from 45 mM to 112 mM. Suitable concentrations of ketorolac in the combination drug compositions of the present invention range from 2 mM to 75 mM, and preferably from 8.5 mM to 24 mM. A buffer system, such as a sodium citrate buffer system, is suitably The amounts of pharmaceutically active ingredients included in the formulation can be expressed in molar ratios. The molar ratio of phenylephrine to ketorolac may range from 1:1 to 13:1, and more suitably may range from 3:1 to 10:1. An exemplary molar ratio of phenylephrine and ketorolac as represented in Table 1 above is 5.4:1 of phenylephrine to ketorolac.

Following dilution of this exemplary formulation of the present invention into an intraocular irrigation carrier for local delivery, the dosing concentration of phenylephrine may be from 3 to 7,200 M, more suitably from 30 to 720 $\mu M$, more preferably from 90 to 720 $\mu M$, still more preferably from 240 to 720 $\mu M$, and most preferably about 483 $\mu M$. Following dilution of the formulation of the present invention into an intraocular irrigation carrier for local delivery, the dosing concentration of ketorolac may be from 3 to 900 $\mu M$, more suitably from 10 to 270 $\mu M$, more preferably from 44 to 134 $\mu M$, still more preferably from 30 to 90 $\mu M$, and most preferably about 90 $\mu M$.

It must be noted that as used herein and in the appended claims, the singular forms "a", "and", and "the" include plural referents unless the context clearly dictates otherwise. Thus, for example, reference to "an excipient" includes a plurality of such excipients and equivalents thereof known to those skilled in the art, and so forth. The term "about" as used herein is understood to mean that there can be variation in a stated condition or amount that can be to 5%, 10%, 15% or up to and including 20% of the given value.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All citations are incorporated herein by reference.

EXAMPLES

Example 1

Clinical Studies Evaluating Phenylephrine 1%/Ketorolac 0.3% in Cataract Surgery and Intraocular Lens Replacement for Maintenance of Mydriasis and Prevention of Postoperative Pain This example describes two Phase 3 clinical studies performed to evaluate the efficacy and safety of phenylephrine 1% and ketorolac 0.3% injection formulated as described in Table 1 above when used for the maintenance of mydriasis during, and prevention of postoperative pain following, cataract surgery and intraocular lens (IOL) replacement.

Methods

Two pivotal, multi-center, randomized, parallel-group, double-masked, placebo-controlled phase 3 studies (Study 1 and Study 2) that were conducted to support the use of phenylephrine 1% and ketorolac 0.3% injection (OMS302) for maintaining intraoperative mydriasis, preventing intraoperative miosis, and reducing early postoperative ocular pain associated with cataract surgery and IOL replacement. A total of 20 sites in the United States and Netherlands enrolled subjects in these studies.

Subjects were randomized to receive either OMS302 or placebo. A single administration of study drug, OMS302 (483 μM phenylephrine and 89 μM ketorolac formulated in 20 mM sodium citrate buffer) or placebo (20 mM sodium citrate buffer), was added to balanced salt solution (BSS, 500 mL) and administered intracamerally as part of the standard irrigation solution during the procedure. Postoperative evaluations were conducted for up to 14 days (Study 1) or 90 days (Study 2); integrated safety analyses were limited to data collected up to 14 days post-surgery. All subjects (OMS302-treated and placebo-treated) in the studies received standard-of-care preoperative topical mydriatic and anesthetic agents.

Two co-primary endpoints were pre-specified for the integrated analyses: 1) intraoperative pupil diameter during surgery and 2) ocular pain during the early postoperative period following surgery. Each subject's surgical procedure was video recorded and change in pupil diameter was measured at one-minute intervals from time of incision (surgical baseline) until wound closure (surgical end) by a single, masked central reader. Postoperative ocular pain was measured using a subject-assessed visual analog scale (VAS) at 2, 4, 6, 8, and 10-12 hours after surgery and on Days 2, 7, and 14.

Key secondary endpoints included pupil diameter<6 mm at end of cortical clean-up, pupil diameter<6 mm at any time during surgery, intraoperative pupillary constriction of ≥2.5 mm, moderate-to-severe ocular pain (VAS≥40) at any time point assessed within the first 12 postoperative hours, and no ocular pain (VAS=0) at all time points assessed within the first 12 postoperative hours. Post-hoc secondary analyses included categorization of subjects' intraoperative pupil constriction and analgesic use on day of surgery.

Statistical Analysis

Each study was conducted independently. The sample size calculations for the two studies were identical: a total of 400 subjects (200 subjects per treatment arm) in each study provided 99% power to detect a difference of 0.6 mm (standard deviation [SD]: 0.7 mm) in mean area-under-the-curve (AUC) pupil diameter change from baseline and 96% power to detect a difference of 5.0 mm (SD: 13.3 mm) in mean AUC of ocular pain VAS during the first 12 postoperative hours using a two-sided t-test with α=0.05.

The mean AUC pupil diameter change from baseline during surgery was calculated as follows: 1) the trapezoidal rule was used to calculate the AUC of the pupil diameter from surgical baseline to wound closure, 2) the result was divided by time of the last pupil diameter value to obtain the mean AUC, and 3) the baseline pupil diameter was subtracted from the mean AUC. The AUC of ocular pain VAS during the first 10-12 postoperative hours was also calculated using the trapezoidal rule with the mean AUC defined as the AUC divided by the number of hours from the first VAS score to the last VAS score within this time frame. For both primary endpoints, a generalized Cochran-Mantel-Haenzel (CMH) test stratified by randomization strata was used to compare the two treatment arms for the two studies combined (LaVange, et al. 2005).

Treatment comparisons for all secondary efficacy analyses presented were performed using Chi-square test or Fisher's exact test if the frequency in a category was less than five. All statistical analyses were performed using SAS software (version 9.3, SAS Institute, Inc., Cary N.C.).

Results—Efficacy

OMS302 was superior to placebo in maintaining mydriasis during cataract surgery or IOL replacement procedures. Among 759 subjects with usable video images for determination of pupil diameter, the mean AUC change-from-baseline in pupil diameter was 0.08 mm for the OMS302 group (n=379) compared to −0.50 mm for the placebo group (n=380) and the CMH-weighted mean difference (OMS302—placebo) (standard error [SE]) was 0.58 mm (0.04) (95% confidence interval [CI]: 0.51, 0.65; p<0.0001). Following initiation of surgery, baseline pupil diameter was maintained with OMS302 treatment while progressive miosis was observed with placebo treatment (FIG. 1). Results of secondary efficacy analyses evaluating incidence of subjects with pupil diameter<6 mm at completion of cortical clean up and at any time during surgery also favored OMS302 treatment (Table 2). The proportions of subjects with pupil diameter<6 mm at the time of cortical clean-up completion, pupil diameter<6 mm at any time during surgery, and degree of intraoperative pupillary constriction of ≥2.5 mm were all significantly lower among OMS302-treated subjects than placebo-treated subjects (p<0.0001 for each endpoint). Considerably fewer OMS302-treated subjects than placebo subjects experienced intraoperative pupil constriction greater than 1 mm (FIG. 2).

TABLE 2

Supportive Efficacy Endpoints

| | Placebo (N = 405) | OMS302 (N = 403) |
|---|---|---|
| Pupil Diameter Endpoints (includes subjects with readable video data) | | |
| Subjects with <6 mm at cortical clean-up | 87/380 (22.9%) | 15/379 (4.0%) |
| p-value[a] | | <0.0001 |
| Subjects with <6 mm at any time during surgery | 161/380 (42.4%) | 37/379 (9.8%) |
| p-value[a] | | <0.0001 |

TABLE 2-continued

Supportive Efficacy Endpoints

|  | Placebo (N = 405) | OMS302 (N = 403) |
|---|---|---|
| Subjects with degree of pupillary constriction[b] | | |
| ≥2.5 mm | 103/380 (27.1%) | 8/379 (2.1%) |
| p-value[a] | | <0.0001 |
| Ocular Pain Endpoints (includes subjects with complete VAS scores) | | |
| Subjects pain free (VAS = 0) at all time points[c] | 69/403 (17.1%) | 104/403 (25.8%) |
| p-value[a] | | 0.0027 |
| Subjects with moderate to severe pain (VAS ≥ 40) at any time point | 57/403 (14.1%) | 29/403 (7.2%) |
| p-value[a] | | 0.0014 |
| Analgesic use on day of surgery | 140/403 (34.7%) | 99/403 (24.6%) |
| p-value[a] | | 0.002 |

[a]Chi-Square test
[b]Maximum decrease in pupil diameter from baseline during surgery
[c]Subjects with missing VAS during 12 hours postoperatively are considered as not being pain-free Treatment with OMS302 was associated with a significant reduction in early postoperative ocular pain compared to placebo. Ocular pain VAS scores during the first 12 hours postoperatively were more than 50% lower for the OMS302 group (mean AUC=4.16 mm, n=403) than for the placebo group (mean AUC=9.06 mm, n=403). The CMH-weighted mean difference (OMS302—placebo) (SE) in AUC of ocular pain scores was −4.89 mm (0.80) (95% CI: −6.46, −3.31; $p<0.001$). Mean VAS scores were lower among subjects treated with OMS302 at each postoperative time point (FIG. 3). The proportion of subjects who were ocular pain free (VAS=0) at all postoperative time points was significantly higher for OMS302 compared to placebo (25.8% vs 17.1%, respectively, p=0.0027; Table 2) and the proportion of subjects with moderate-to-severe ocular pain (VAS≥40) at any postoperative time point was significantly lower for OMS302 compared to placebo (7.2% vs 14.1%, respectively, p=0.0014). Notably, in addition to lower VAS pain scores in the OMS302 group, use of analgesics on the day of surgery was also significantly lower among subjects treated with OMS302 compared to placebo (24.6% vs 35.1%, respectively, p=0.0010).

Results—Safety

Of the 808 subjects (403 OMS302, 405 placebo) included in the pooled safety analyses, 513 (63.5%) experienced at least one treatment-emergent adverse event (TEAE). The proportion of subjects reporting TEAEs was slightly lower among subjects receiving OMS302 (242/403 [60.0%]) than placebo (271/405 [66.9%]). The majority of TEAEs were mild or moderate in severity. Only one serious adverse event was reported in the two studies. This event (death due to electrocution deemed unrelated to study drug) was also the only event that resulted in premature discontinuation from the studies.

The most frequently-reported TEAE consisted of eye pain (reported by 35.1% of subjects overall), eye inflammation (15.5%), anterior chamber inflammation (8.7%), headache (7.9%), intraocular pressure increased (4.1%), posterior capsule opacification (4.1%), ocular discomfort (4.1%), photophobia (4.0%), corneal edema (2.8%), vision blurred (2.7%), conjunctival hyperemia (2.6%), and foreign body sensation in the eyes (2.2%). These events were reported by similar proportions of subjects in each treatment group with the exception of eye pain, headache, ocular discomfort, photophobia, and vision blurred, which were experienced by slightly more (>1% difference between treatment groups) placebo subjects (40.0%, 9.4%, 5.2%, 4.9%, 4.2%, respectively) than OMS302 subjects (30.3%, 6.5%, 3.0%, 3.0%, 1.2%, respectively). Increased intraocular pressure was the only common TEAE occurring in a slightly greater proportion (>1% difference) of OMS302-treated subjects (4.7°% OMS302 vs 3.5% placebo).

Severe TEAEs were experienced by a total of 18 subjects (13 [3.2%] placebo subjects and 5 [1.2%] OMS302 subjects). Except for the event of accidental electrocution experienced by a subject treated with OMS302, all severe TEAEs consisted of eye disorders, including eye inflammation (n=11), anterior chamber inflammation (n=2), and conjunctival edema, corneal edema, conjunctival hyperemia, eye pain, and photophobia (n=1 each). Of note, all severe TEAEs considered to be related to study treatment occurred among subjects receiving placebo. These events included two instances of anterior chamber inflammation, and events of, corneal edema, eye pain, photophobia, eye inflammation, and conjunctival hyperemia.

Increased intraocular pressure was observed for several subjects in both treatment groups following surgery. By Day 2, increases compared to baseline were less notable; however, the abnormality persisted in some subjects through the end of the study. No notable TEAEs were reported in these subjects and no differences in the proportions of subjects with increased intraocular pressure were observed between the two treatment groups on each evaluation day. In addition, no differences between treatment groups were observed for any other serial assessments of safety (i.e., vital signs or ophthalmological exams).

Conclusions

OMS302 was superior to placebo for the maintenance of mydriasis during, and reduction of ocular pain following, IOL replacement. The mean area-under-the-curve (AUC) change from baseline in pupil diameter was 0.08 mm for OMS302 compared to −0.50 mm for placebo (p<0.0001). Mean AUC of subject ocular pain visual analog scale (VAS) scores within 12 hours postoperatively were over 50% lower for OMS302 (mean AUC=4.16 mm) than placebo (mean AUC=9.06 mm, p<0.001). Results of all secondary efficacy analyses demonstrated a significant treatment effect associated with OMS302. Treatment-emergent adverse events were as expected for a population undergoing IOL replacement; no clinically significant differences in safety measures were observed between treatment groups.

The integrated results of these two pivotal phase 3 studies demonstrate the superiority of OMS302 compared to placebo in maintaining pupil diameter and preventing miosis during, and preventing postoperative ocular pain following, cataract extraction with lens replacement or refractive lens exchange procedures, even though all subjects received standard preoperative topical mydriatics and anesthetics. The efficacy analyses were robust; AUC analyses of the co-primary endpoints for the integrated analysis, performed to show the aggregate effect of OMS302 on pupil diameter during surgery and early postoperative pain, and all secondary efficacy analyses were supportive. Furthermore, OMS302 was not associated with any new or additional toxicities compared to placebo. Common adverse events and safety findings (e.g., increased intraocular pressure) observed in clinical studies of OMS302 performed to date are consistent with events commonly reported among patients undergoing these procedures, and no clinically significant differences between treatment groups were observed.

Example 2

Ocular Tissue Distribution of Ketorolac Following Administration of Phenylephrine 1%/Ketorolac 0.3% to Dogs During Intraocular Lens Replacement This example describes the results of an in vivo study in dogs to determine the concentrations of ketorolac in the retina and other ocular tissues following the intracameral administration of phenylephrine 1% and ketorolac 0.3% injection formulated as described in Table 1 (OMS302) during IOL replacement in dogs.

Methods

IOL replacement by phacoemulsification was performed on 20 female beagles. During the procedure, OMS302 was administered in BSS solution via irrigation and intracameral injection immediately post-procedure. The target dose level of ketorolac was 5.71 mg/eye, and the target dose volume of OMS302 diluted in BSS solution was 250 mL per eye. Four animals per time point were sacrificed at 0, 2, 6, 8, and 10 hours post-procedure. Samples of blood and aqueous humor were collected. Enucleated eyes were frozen and dissected for collection of retina, retinal pigmented epithelium-choroid, cornea, iris-ciliary body, vitreous humor, sclera, and lens capsule. Tissue concentrations of ketorolac were quantitated using a liquid chromatography/mass spectrometry (LCMS) method. Using published IC50 values for cyclooxygenase (COX) inhibition by ketorolac (Waterbury, et. al., *Curr Med Res Opin* 22(6):1133-40 (2006)), estimates of percent inhibition were derived for each time point.

Results

FIGS. 4-6 illustrate the mean concentrations of ketorolac at specified time points after the intracameral doses of OMS302, with FIG. 4 showing ketorolac concentrations in the cornea, lens capsule, iris-ciliary body (ICB), aqueous humor, and anterior sclera; FIG. 5 showing ketorolac concentrations in the bulbar and palpebral conjunctiva; and FIG. 6 showing the ketorolac concentrations in vitreous humor, retina, choroid-RPE (peripheral), choroid-RPE (tapetum), and posterior sclera. FIG. 7 shows the mean percent inhibition of COX-1 and COX-2 in retinal tissues at t=0 through t=10 hours, based on an IC50 of 20 nM and a Ki of 10 nM for COX-1 and an IC50 of 120 nM and a Ki of 60 nM for COX-2. Ketorolac concentrations in the retina were 1400±1004 ng/g immediately following the end of IOL replacement, and 164±39 ng/g at eight hours post-procedure, corresponding to estimated COX-1/COX-2 inhibition of 99.3%/96.0% at t=0, and 98.4%/91.1% at t=8 hours. The retinal half-life was ~3.8 hours. Surprisingly, tissue concentrations in aqueous humor, vitreous humor, and RPE-choroid at t=8 hours were consistent with >90% inhibition of COX-1 and COX-2. Also surprisingly, at t=10 hours, retinal tissue concentrations were 97.74% (with a standard deviation of 0.36%) for COX-1 and 87.82 (with a standard deviation of 1.75%) for COX-2. The mean plasma level of ketorolac was 4.73±1.46 ng/mL at t=0, declining to undetectable levels at t≥2 hours.

Conclusions

In this study, the use of OMS302 during IOL replacement surgery resulted in the uptake of ketorolac by retina and other ocular tissues at levels sufficient to inhibit COX-1 and COX-2 levels in intraocular tissues by greater than 90% for at least 8 hours, and by greater than 85% for at least 10 hours, following drug administration in the intracameral irrigation solution, which duration of action was unexpected. Systemic exposure was low and transient.

Example 3

Clinical Study Evaluating Intracameral Ketorolac Concentration Following Topical Ketorolac Administration Prior to Cataract Surgery This example describes the results of a clinical study to determine postoperative intracameral concentrations of ketorolac in subjects receiving topical ketorolac prior to cataract surgery.

Methods

Patients undergoing cataract extraction and lens replacement (CELR) were eligible. Written informed consent was obtained from 14 subjects, each of whom received topical ophthalmic ketorolac according to the surgeon's usual practice, beginning one day preoperatively. Immediately prior to the initial surgical incision, the surgeon withdrew a 100-µL sample of aqueous humor from the operative eye with a 30-gauge tuberculin syringe. At the conclusion of CELR prior to final re-inflation of the anterior chamber and wound closure, the surgeon withdrew another 100-µL sample from the anterior chamber. The ketorolac concentrations of the intracameral fluid samples were analyzed by an analytical laboratory.

Results

Thirteen of 14 subjects used four doses of ketorolac the day prior to surgery, and one subject used three doses the day prior to surgery. All 14 subjects received topical ketorolac in the surgery center on the day of surgery. Aqueous humor samples were inadvertently not collected from two subjects. The preoperative ketorolac concentrations for the 12 subjects on whom samples were collected ranged from 4.9 to 369 ng/mL. The end-of-procedure samples ranged from <1.0 (the lower limits of quantification, or LLOQ) to 6.32 ng/mL, with eight of the 12 subjects having ketorolac levels below the LLOQ.

Conclusions

At-home compliance with topical ketorolac was generally good, with 92.9% of subjects using topical ketorolac as directed. Following CELR, levels of ketorolac in the aqueous humor at the end of the surgical procedure were low, likely due to irrigation wash-out, as 66.7% of subjects had an undetectable concentration of ketorolac.

The in vim and clinical studies of Examples 2 and 3, respectively, demonstrate that intracamerally delivering ketorolac in a ketorolac/phenylephrine solution during cataract and IOL replacement surgery should result in a pharmacologically active level of ketorolac in the eye for a substantially longer postoperative time than results from topically delivering ketorolac preoperatively, thereby providing for sustained postoperative inflammation inhibition.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The embodiments of the invention in which an exclusive property or privilege is claimed are defined as follows:

1. A method for reducing the incidence or severity of postoperative cystoid macular edema following an ophthalmologic surgical procedure in a subject with an elevated risk of suffering from a postoperative cystoid macular edema, the method comprising:
- administering intracamerally to the subject during an ophthalmologic surgical procedure an effective amount of a solution including a nonsteroidal anti-inflammatory drug (NSAID) and an alpha-1 adrenergic receptor agonist mydriatic agent in an intraocular irrigation carrier, wherein the effective amount is the amount of the solution is sufficient for uptake of an amount of the NSAID in ocular tissues sufficient for at least 90% inhibition of baseline cyclooxygenase-1 and cyclooxygenase-2 activity levels in ocular tissues for a period of at least eight hours postoperatively,
- wherein the NSAID is ketorolac and the mydriatic agent is phenylephrine, and
- wherein the subject with an elevated risk of suffering from a postoperative cystoid macular edema is over 65 years of age or has diabetes mellitus.

2. The method of claim 1, wherein the solution comprises phenylephrine at a concentration of from 240 to 720 μM and the ketorolac is present at a concentration of from 44 to 134 μM.

3. The method of claim 1, wherein a sufficient amount of the NSAID and the mydriatic agent are included in the solution to maintain an intraoperative pupil diameter of at least 6.0 mm during the procedure.

4. The method of claim 1, wherein the solution is administered by continuous intracameral irrigation during the procedure.

5. The method of claim 4, wherein the solution is administered by continuous intracameral irrigation during the procedure followed by injection of a bolus of the solution at the end of the procedure.

6. The method of claim 1, wherein the solution is administered by intracameral injection during a procedure in which another therapeutic agent is injected intraocularly.

* * * * *